US009186133B2

(12) United States Patent
Gregoire et al.

(10) Patent No.: US 9,186,133 B2
(45) Date of Patent: Nov. 17, 2015

(54) BONE ANCHOR INSERTION DEVICE

(75) Inventors: David Gregoire, Mission Viejo, CA (US); George White, Corona, CA (US); Minh Tran, Fountain Valley, CA (US); Seth Foerster, San Clemente, CA (US)

(73) Assignee: ArthroCare Corporation, Austin, TX (US)

( * ) Notice: Subject to any disclaimer, the term of this patent is extended or adjusted under 35 U.S.C. 154(b) by 632 days.

(21) Appl. No.: 12/904,534

(22) Filed: Oct. 14, 2010

(65) Prior Publication Data
US 2011/0028997 A1 Feb. 3, 2011

Related U.S. Application Data

(60) Continuation of application No. 10/885,282, filed on Jul. 6, 2004, now abandoned, which is a division of application No. 10/077,574, filed on Feb. 15, 2002, now Pat. No. 6,780,198.

(60) Provisional application No. 60/338,429, filed on Dec. 6, 2001.

(51) Int. Cl.
*A61B 17/04* (2006.01)

(52) U.S. Cl.
CPC ....... *A61B 17/0401* (2013.01); *A61B 2017/045* (2013.01); *A61B 2017/0409* (2013.01); *A61B 2017/0435* (2013.01); *A61B 2017/0496* (2013.01)

(58) Field of Classification Search
CPC ........... A61B 17/0401; A61B 17/0409; A61B 2017/0496; A61B 17/0485; A61B 2017/0488

USPC .......... 606/72, 73, 96, 104, 148, 232, 144, 14
See application file for complete search history.

(56) References Cited

U.S. PATENT DOCUMENTS

| 918,570 A | 4/1909 | Mather ........................ 292/318 |
| 919,138 A | 4/1909 | Drake et al. .................. 606/144 |
| 1,153,053 A | 9/1915 | Forster ........................ 43/44.85 |

(Continued)

FOREIGN PATENT DOCUMENTS

| DE | 025 32 242 A1 | 2/1977 | ............. A61B 17/06 |
| DE | 042 35 602 A1 | 4/1994 | ............. A61B 17/04 |

(Continued)

OTHER PUBLICATIONS

PCT International Search Report for PCT/US02/38632 2 pgs, Mailed May 16, 2003.

(Continued)

*Primary Examiner* — Diane Yabut
(74) *Attorney, Agent, or Firm* — Norman F. Hainer, Jr.

(57) ABSTRACT

A bone anchor insertion device is disclosed for attaching a suture that is fixed to portion of soft tissue to a portion of bone. The device has a handle, a nosepiece connected to a distal end of the handle, a bone anchor connected to the nosepiece, and an actuator disposed on the handle for deploying the bone anchor. A suture ratchet or tensioning mechanism is disposed in the handle for tensioning suture which is associated with the bone anchor. This mechanism permits precise tensioning, while also permitting one-handed operation, thereby allowing the practitioner to use his or her other hand for other activities, such as camera operation or the like.

23 Claims, 15 Drawing Sheets

(56) References Cited

U.S. PATENT DOCUMENTS

| | | | |
|---|---|---|---|
| 1,565,041 A | 12/1925 | Arneu | 24/129 R |
| 2,269,963 A | 1/1942 | Wrapler | 604/61 |
| 2,286,578 A | 6/1942 | Sauter | 606/144 |
| 2,600,395 A | 6/1952 | Domoj et al. | 87/13 |
| 3,143,916 A | 8/1964 | Rice | 85/71 |
| 3,946,740 A | 3/1976 | Bassett | 128/334 |
| 3,994,521 A | 11/1976 | Van Gompel | 292/319 |
| 4,047,533 A | 9/1977 | Perciaccante et al. | 128/335.5 |
| 4,109,658 A | 8/1978 | Hughes | 128/340 |
| 4,164,225 A | 8/1979 | Johnson et al. | 128/334 |
| 4,186,921 A | 2/1980 | Fox | 29/461 |
| 4,301,551 A | 11/1981 | Dore et al. | 623/13.3 |
| 4,319,428 A | 3/1982 | Fox | 47/42 |
| 4,345,601 A | 8/1982 | Fukuda | 128/339 |
| 4,373,530 A | 2/1983 | Kilejian | 128/334 R |
| 4,384,389 A | 5/1983 | Sato | 24/136 K |
| 4,409,974 A | 10/1983 | Freedland | 128/92 |
| 4,456,270 A | 6/1984 | Zettl et al. | 279/62 |
| 4,467,478 A | 8/1984 | Jurgutis | 606/75 |
| 4,483,023 A | 11/1984 | Hoffman, Jr. et al. | 623/13.15 |
| 4,493,323 A | 1/1985 | Albright et al. | 128/340 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | 411/340 |
| 4,672,957 A | 6/1987 | Hourahane | 606/80 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,772,286 A | 9/1988 | Goble et al. | 623/13.14 |
| 4,779,616 A | 10/1988 | Johnson et al. | 606/148 |
| 4,781,182 A | 11/1988 | Purnell et al. | 128/92 |
| 4,792,336 A | 12/1988 | Hlavacek et al. | 623/13.18 |
| 4,809,408 A | 3/1989 | Abrahamson | 24/136 K |
| 4,823,780 A | 4/1989 | Odensten et al. | 606/96 |
| 4,828,439 A | 5/1989 | Giannuzzi | 411/37 |
| 4,834,755 A | 5/1989 | Silvestrini et al. | 623/13.19 |
| 4,836,205 A | 6/1989 | Barrett | 128/340 |
| 4,917,700 A | 4/1990 | Aikins | 623/13.19 |
| 4,923,461 A | 5/1990 | Caspari | 606/146 |
| 4,926,860 A | 5/1990 | Stice et al. | 606/144 |
| 4,935,027 A | 6/1990 | Yoon | 606/146 |
| 4,946,377 A | 8/1990 | Kovach | 623/13.18 |
| 4,946,467 A | 8/1990 | Ohi et al. | 606/228 |
| 4,946,468 A | 8/1990 | Li | 606/232 |
| 4,957,498 A | 9/1990 | Caspari et al. | 606/146 |
| 4,962,929 A | 10/1990 | Melton, Jr. | 473/516 |
| 4,981,149 A | 1/1991 | Yoon et al. | 128/898 |
| 4,987,665 A | 1/1991 | Dumican | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst | 606/72 |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | 411/29 |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | 623/13.14 |
| 5,217,495 A | 6/1993 | Kaplan et al. | 623/13.18 |
| 5,222,977 A | 6/1993 | Esser | 606/223 |
| 5,224,946 A | 7/1993 | Hayhurst | 606/72 |
| 5,259,846 A | 11/1993 | Granger et al. | 606/224 |
| 5,263,984 A | 11/1993 | Li et al. | 623/13.18 |
| 5,275,176 A | 1/1994 | Chandler | 606/242 |
| 5,304,184 A | 4/1994 | Hathaway et al. | 606/144 |
| 5,312,422 A | 5/1994 | Trott | 606/144 |
| 5,318,575 A | 6/1994 | Chesterfield et al. | 606/151 |
| 5,324,308 A | 6/1994 | Pierce | 606/232 |
| 5,326,205 A | 7/1994 | Anspach, III et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | 606/72 |
| 5,364,407 A | 11/1994 | Poll | 606/139 |
| 5,376,118 A | 12/1994 | Kaplan et al. | 623/23.72 |
| 5,383,905 A | 1/1995 | Gold et al. | 606/232 |
| 5,397,325 A | 3/1995 | Della Badia et al. | 606/144 |
| 5,405,352 A | 4/1995 | Weston | 606/148 |
| 5,405,359 A | 4/1995 | Pierce | 606/232 |
| 5,409,494 A | 4/1995 | Morgan | 606/96 |
| 5,417,691 A | 5/1995 | Hayhurst | 606/72 |
| 5,417,699 A | 5/1995 | Klein et al. | 606/139 |
| 5,417,712 A | 5/1995 | Whittaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | 606/232 |
| 5,470,335 A | 11/1995 | DuToit | 606/73 |
| 5,472,452 A | 12/1995 | Trott | 606/232 |
| 5,474,565 A | 12/1995 | Trott | 606/144 |
| 5,480,403 A | 1/1996 | Lee et al. | 606/72 |
| 5,486,197 A | 1/1996 | Le et al. | 606/232 |
| 5,499,991 A | 3/1996 | Garman et al. | 606/148 |
| 5,501,683 A | 3/1996 | Trott | 606/72 |
| 5,501,695 A | 3/1996 | Anspach, Jr. et al. | 606/232 |
| 5,505,735 A | 4/1996 | Li | 606/72 |
| 5,514,159 A | 5/1996 | Matula et al. | 606/232 |
| 5,520,700 A | 5/1996 | Beyar et al. | 606/139 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | 606/232 |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | 606/73 |
| 5,584,839 A | 12/1996 | Gieringer | 606/96 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | 606/72 |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,552 A | 7/1997 | Sherts | 606/145 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,658,313 A | 8/1997 | Thal | 606/232 |
| 5,665,108 A | 9/1997 | Galindo | 606/215 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | D24/145 |
| 5,681,333 A | 10/1997 | Burkhart et al. | 606/148 |
| 5,681,351 A | 10/1997 | Jamiolkowski | 606/232 |
| 5,683,417 A | 11/1997 | Cooper | 606/223 |
| 5,683,418 A | 11/1997 | Luscombe et al. | 606/232 |

(56) References Cited

U.S. PATENT DOCUMENTS

| | | | | |
|---|---|---|---|---|
| 5,683,419 | A | 11/1997 | Thal | 606/232 |
| 5,690,649 | A | 11/1997 | Li | 606/139 |
| 5,693,060 | A | 12/1997 | Martin | 606/148 |
| 5,697,950 | A | 12/1997 | Fucci et al. | 606/232 |
| 5,702,397 | A * | 12/1997 | Goble et al. | 606/232 |
| 5,702,398 | A | 12/1997 | Tarabishy | 606/72 |
| 5,707,362 | A | 1/1998 | Yoon | 604/164 |
| 5,707,394 | A | 1/1998 | Miller et al. | 606/232 |
| 5,709,708 | A | 1/1998 | Thal | 606/232 |
| 5,720,765 | A | 2/1998 | Thal | 606/232 |
| 5,725,541 | A | 3/1998 | Anspach, III et al. | 606/151 |
| 5,728,136 | A | 3/1998 | Thal | 606/232 |
| 5,733,307 | A | 3/1998 | Dinsdale | 606/232 |
| 5,741,281 | A | 4/1998 | Martin | 606/148 |
| 5,741,282 | A | 4/1998 | Anspach, III et al. | 606/151 |
| 5,766,250 | A | 6/1998 | Chervitz et al. | 623/13 |
| 5,776,150 | A | 7/1998 | Nolan et al. | 606/148 |
| 5,779,719 | A | 7/1998 | Klein et al. | 606/144 |
| 5,782,863 | A | 7/1998 | Bartlett | 606/232 |
| 5,782,864 | A | 7/1998 | Lizardi | 606/232 |
| 5,782,865 | A | 7/1998 | Grotz | 606/72 |
| 5,791,899 | A | 8/1998 | Sachdeva | 433/173 |
| 5,792,152 | A | 8/1998 | Klein et al. | 606/144 |
| 5,792,153 | A | 8/1998 | Swain et al. | 606/144 |
| 5,797,927 | A | 8/1998 | Yoon | 606/144 |
| 5,797,963 | A | 8/1998 | McDevitt | 606/232 |
| 5,810,848 | A | 9/1998 | Hayhurst | 606/144 |
| 5,810,854 | A | 9/1998 | Beach | 606/151 |
| 5,814,052 | A | 9/1998 | Nakao et al. | 606/148 |
| 5,814,056 | A | 9/1998 | Prosst et al. | 606/151 |
| 5,814,071 | A | 9/1998 | McDevitt et al. | 606/232 |
| 5,814,072 | A | 9/1998 | Bonutti | 606/232 |
| 5,843,111 | A | 12/1998 | Vijfvinkel | 606/171 |
| 5,849,004 | A | 12/1998 | Bramlet | 606/232 |
| 5,860,978 | A | 1/1999 | McDevitt | 606/72 |
| 5,860,991 | A | 1/1999 | Klein et al. | 606/144 |
| 5,860,992 | A | 1/1999 | Daniel et al. | 606/145 |
| 5,868,789 | A | 2/1999 | Huebner | 606/232 |
| 5,879,372 | A | 3/1999 | Bartlett | 606/232 |
| 5,882,340 | A | 3/1999 | Yoon | 604/164 |
| 5,885,294 | A | 3/1999 | Pedlick et al. | 606/80 |
| 5,891,168 | A | 4/1999 | Thal | 606/232 |
| 5,893,850 | A | 4/1999 | Cachia | 606/72 |
| 5,902,311 | A | 5/1999 | Andreas et al. | 606/144 |
| 5,904,692 | A | 5/1999 | Steckel et al. | 606/139 |
| 5,906,624 | A * | 5/1999 | Wenstrom, Jr. | 606/139 |
| 5,911,721 | A | 6/1999 | Nicholson et al. | 606/72 |
| 5,921,994 | A | 7/1999 | Andreas et al. | 606/144 |
| 5,935,129 | A | 8/1999 | Mdevitt | 606/72 |
| 5,941,900 | A | 8/1999 | Bonutti | 606/232 |
| 5,941,901 | A | 8/1999 | Egan | 606/232 |
| 5,944,724 | A | 8/1999 | Lizardi | 606/104 |
| 5,947,982 | A | 9/1999 | Duran | 606/139 |
| 5,948,000 | A | 9/1999 | Larsen et al. | 606/232 |
| 5,948,001 | A | 9/1999 | Larsen | 606/232 |
| 5,948,002 | A | 9/1999 | Bonutti | 606/232 |
| 5,957,953 | A | 9/1999 | DiPoto et al. | 606/232 |
| 5,957,968 | A | 9/1999 | Belden et al. | 607/126 |
| 5,961,530 | A | 10/1999 | Moore et al. | 606/148 |
| 5,961,538 | A | 10/1999 | Pedlick et al. | 606/232 |
| 5,968,044 | A | 10/1999 | Nicholson et al. | 606/72 |
| 5,980,558 | A | 11/1999 | Wiley | 606/232 |
| 5,980,559 | A | 11/1999 | Bonutti | 606/232 |
| 5,984,933 | A | 11/1999 | Yoon | 606/144 |
| 5,993,459 | A | 11/1999 | Larsen | 606/104 |
| 6,001,104 | A | 12/1999 | Benderev et al. | 606/80 |
| 6,001,109 | A | 12/1999 | Kontos | 606/148 |
| 6,007,566 | A | 12/1999 | Wenstrom, Jr. | 606/232 |
| 6,007,567 | A | 12/1999 | Bonutti | 606/232 |
| 6,010,525 | A | 1/2000 | Bonutti et al. | 606/232 |
| 6,013,083 | A | 1/2000 | Bennett | 606/104 |
| 6,017,346 | A | 1/2000 | Grotz | 606/72 |
| 6,022,360 | A | 2/2000 | Reimels et al. | 606/144 |
| 6,022,373 | A | 2/2000 | Li | 606/232 |
| 6,024,758 | A | 2/2000 | Thal | 606/232 |
| 6,033,430 | A | 3/2000 | Bonutti | 606/232 |
| 6,036,699 | A | 3/2000 | Andreas et al. | 606/139 |
| 6,045,571 | A | 4/2000 | Hill et al. | 606/228 |
| 6,045,572 | A | 4/2000 | Johnson et al. | 606/232 |
| 6,045,574 | A | 4/2000 | Thal | 606/232 |
| 6,048,351 | A | 4/2000 | Gordon et al. | 606/144 |
| 6,051,006 | A | 4/2000 | Shluzas et al. | 606/148 |
| 6,053,935 | A | 4/2000 | Brenneman et al. | 606/232 |
| 6,056,773 | A | 5/2000 | Bonutti | 606/232 |
| 6,066,146 | A | 5/2000 | Carroll et al. | 606/148 |
| 6,068,648 | A | 5/2000 | Cole et al. | 606/232 |
| 6,083,243 | A | 7/2000 | Pokropinski et al. | 606/230 |
| 6,086,608 | A | 7/2000 | Elk et al. | 606/232 |
| 6,096,051 | A | 8/2000 | Kortenbach et al. | 606/144 |
| 6,102,934 | A | 8/2000 | Li | 606/232 |
| 6,117,160 | A | 9/2000 | Bonutti | 606/215 |
| 6,117,161 | A | 9/2000 | Li | 606/232 |
| 6,143,004 | A | 11/2000 | Davis et al. | 606/144 |
| 6,146,386 | A | 11/2000 | Blackman | 606/103 |
| 6,146,406 | A | 11/2000 | Shluzas et al. | 606/232 |
| 6,149,669 | A | 11/2000 | Li | 606/232 |
| 6,156,039 | A | 12/2000 | Thal | 606/72 |
| 6,156,056 | A | 12/2000 | Kearns et al. | 606/232 |
| 6,159,235 | A | 12/2000 | Kim | 606/232 |
| 6,162,537 | A | 12/2000 | Martin et al. | 428/373 |
| 6,165,204 | A | 12/2000 | Levinson et al. | 606/232 |
| 6,171,317 | B1 | 1/2001 | Jackson et al. | 606/148 |
| 6,174,324 | B1 * | 1/2001 | Egan et al. | 606/232 |
| 6,200,329 | B1 | 3/2001 | Fung et al. | 606/232 |
| 6,206,895 | B1 | 3/2001 | Levinson | 606/144 |
| 6,214,028 | B1 | 4/2001 | Yoon et al. | 606/205 |
| 6,217,592 | B1 | 4/2001 | Freda et al. | 606/145 |
| 6,228,096 | B1 * | 5/2001 | Marchand | 606/139 |
| 6,241,736 | B1 | 6/2001 | Sater | 606/104 |
| 6,267,766 | B1 | 7/2001 | Burkhart | 606/72 |
| 6,280,474 | B1 | 8/2001 | Cassidy et al. | 623/16.11 |
| 6,293,961 | B2 | 9/2001 | Schwartz | 606/232 |
| 6,315,781 | B1 | 11/2001 | Reinhardt | 606/108 |
| 6,319,252 | B1 | 11/2001 | McDevitt et al. | 606/60 |
| 6,319,269 | B1 | 11/2001 | Li | 606/232 |
| 6,319,271 | B1 | 11/2001 | Schwartz | 606/232 |
| 6,328,758 | B1 | 12/2001 | Tornier et al. | 606/232 |
| 6,355,053 | B1 | 3/2002 | Li | 606/232 |
| 6,409,743 | B1 | 6/2002 | Fenton | 606/232 |
| 6,436,109 | B1 | 8/2002 | Kontos | 606/148 |
| 6,451,030 | B2 * | 9/2002 | Li et al. | 606/139 |
| 6,464,713 | B2 | 10/2002 | Bonutti | 606/232 |
| 6,471,715 | B1 * | 10/2002 | Weiss | 606/216 |
| 6,475,230 | B1 | 11/2002 | Bonutti et al. | 606/232 |
| 6,517,542 | B1 | 2/2003 | Papay et al. | 606/73 |
| 6,520,980 | B1 | 2/2003 | Foerster | 606/232 |
| 6,524,317 | B1 | 2/2003 | Ritchart et al. | 606/72 |
| 6,527,794 | B1 | 3/2003 | McDevitt et al. | 606/232 |
| 6,533,796 | B1 | 3/2003 | Sauer et al. | 606/144 |
| 6,540,770 | B1 | 4/2003 | Tornier et al. | 606/232 |
| 6,551,330 | B1 | 4/2003 | Bain et al. | 606/144 |
| 6,569,187 | B1 | 5/2003 | Bonutti et al. | 606/232 |
| 6,575,987 | B2 | 6/2003 | Gellman et al. | 606/151 |
| 6,582,453 | B1 | 6/2003 | Tran et al. | 606/232 |
| 6,585,730 | B1 | 7/2003 | Foerster | 606/232 |
| 6,635,073 | B2 | 10/2003 | Bonutti | 606/232 |
| 6,638,279 | B2 | 10/2003 | Bonutti | 606/60 |
| 6,645,227 | B2 | 11/2003 | Fallin et al. | 606/232 |
| 6,652,561 | B1 | 11/2003 | Tran | 606/232 |
| 6,656,183 | B2 | 12/2003 | Colleran | 606/72 |
| 6,660,008 | B1 | 12/2003 | Foerster et al. | 606/72 |
| 6,660,023 | B2 | 12/2003 | McDevitt et al. | 606/232 |
| 6,679,896 | B2 | 1/2004 | Gellman et al. | 606/148 |
| 6,682,549 | B2 | 1/2004 | Bartlett | 606/232 |
| 6,689,154 | B2 | 2/2004 | Bartlett | 606/232 |
| 6,692,516 | B2 | 2/2004 | West et al. | 606/232 |
| 6,712,830 | B2 | 3/2004 | Esplin | 606/152 |
| 6,716,234 | B2 | 4/2004 | Grafton et al. | 606/228 |
| 6,716,490 | B2 | 4/2004 | Hayashi et al. | 606/228 |
| 6,736,829 | B1 | 5/2004 | Li et al. | 606/232 |
| 6,770,076 | B2 | 8/2004 | Foerster | 606/72 |
| 6,780,198 | B1 | 8/2004 | Gregoire et al. | 606/232 |
| 6,855,157 | B2 | 2/2005 | Foerster et al. | 606/232 |
| 6,860,887 | B1 | 3/2005 | Frankie | 606/104 |

(56) References Cited

U.S. PATENT DOCUMENTS

| | | |
|---|---|---|
| 6,972,027 B2 | 12/2005 | Fallin et al. .................. 606/232 |
| 7,029,482 B1 | 4/2006 | Vargas et al. ................. 606/153 |
| 7,029,490 B2 | 4/2006 | Grafton ........................ 606/228 |
| 7,083,638 B2 | 8/2006 | Foerster ....................... 606/232 |
| 7,087,064 B1 | 8/2006 | Hyde ........................... 606/142 |
| 7,090,690 B2 | 8/2006 | Foerster et al. .............. 606/232 |
| 7,144,415 B2 | 12/2006 | Del Rio et al. ............... 606/232 |
| 7,150,750 B2 | 12/2006 | Damarati .................... 623/17.11 |
| 7,320,701 B2 | 1/2008 | Haut et al. ................... 606/232 |
| 7,329,272 B2 | 2/2008 | Burkhart et al. ............. 606/232 |
| 7,410,489 B2 | 8/2008 | Dakin et al. ................. 606/103 |
| 7,527,590 B2 | 5/2009 | Suzuki et al. ................ 600/104 |
| 7,588,587 B2 | 9/2009 | Barbieri et al. .............. 606/232 |
| 7,615,061 B2 | 11/2009 | White et al. ................. 606/148 |
| 7,806,909 B2 | 10/2010 | Fallin et al. .................. 606/232 |
| 7,867,251 B2 | 1/2011 | Colleran et al. .............. 606/232 |
| 7,963,972 B2 | 6/2011 | Foerster et al. .............. 606/139 |
| 7,981,140 B2 | 7/2011 | Burkhart ....................... 606/232 |
| 8,105,355 B2 | 1/2012 | Page et al. .................... 606/232 |
| 8,133,258 B2 | 3/2012 | Foerster et al. .............. 606/232 |
| 8,317,829 B2 | 11/2012 | Foerster et al. .............. 606/232 |
| 2003/0167062 A1 | 9/2003 | Gambale ...................... 606/232 |
| 2004/0138683 A1 | 7/2004 | Shelton et al. ............... 606/151 |
| 2004/0153074 A1 | 8/2004 | Bojarski et al. .............. 606/232 |
| 2005/0033364 A1 | 2/2005 | Gregoire et al. .............. 606/232 |
| 2005/0090827 A1 | 4/2005 | Gedebou ....................... 606/72 |
| 2005/0131430 A1 | 6/2005 | Ravikumar ................... 606/144 |
| 2005/0277986 A1 | 12/2005 | Foerster ....................... 606/232 |
| 2006/0079904 A1 | 4/2006 | Thal .............................. 606/72 |
| 2006/0161159 A1 | 7/2006 | Dreyfuss et al. .............. 606/72 |
| 2006/0161183 A1 | 7/2006 | Sauer ........................... 606/148 |
| 2006/0271060 A1 | 11/2006 | Gordon ........................ 606/232 |
| 2006/0271105 A1 | 11/2006 | Foerster ........................ 606/232 |
| 2006/0293710 A1 | 12/2006 | Foerster ........................ 606/72 |
| 2007/0055379 A1 | 3/2007 | Stone et al. ................... 606/75 |
| 2007/0142838 A1 | 6/2007 | Jordan ........................... 606/75 |
| 2008/0051836 A1 | 2/2008 | Foerster et al. .............. 606/232 |
| 2008/0154286 A1 | 6/2008 | Abbott et al. ................. 606/139 |
| 2009/0048613 A1 | 2/2009 | Surti ............................. 606/139 |
| 2009/0069823 A1 | 3/2009 | Foerster et al. .............. 606/103 |
| 2009/0326562 A1 | 12/2009 | White et al. .................. 606/148 |
| 2009/0326563 A1 | 12/2009 | White et al. .................. 606/148 |
| 2009/0326564 A1 | 12/2009 | White et al. .................. 606/148 |
| 2012/0095507 A1 | 4/2012 | White et al. .................. 606/232 |

FOREIGN PATENT DOCUMENTS

| | | | |
|---|---|---|---|
| DE | 196 28 909 A1 | 1/1998 | ............ A61B 17/04 |
| EP | 0 535 906 A2 | 4/1993 | ............ A61B 17/04 |
| EP | 0 571 686 A1 | 12/1993 | ............ A61B 2/08 |
| EP | 1 072 234 A2 | 1/2001 | ............ A61F 2/08 |
| EP | 1 072 237 A1 | 1/2001 | ............ A61F 2/36 |
| EP | 1987779 | 11/2008 | ............ A61B 17/04 |
| GB | 2452825 | 3/2009 | ............ A61B 17/04 |
| JP | 2286468 | 11/1990 | ............ B62D 1/16 |
| WO | 91/06247 | 5/1991 | ............ A61B 17/00 |
| WO | 95/06439 | 3/1995 | ............ A61B 17/00 |
| WO | 95/25469 | 9/1995 | ............ A61B 17/04 |
| WO | 96/17544 | 6/1996 | ............ A61B 17/04 |
| WO | 98/07374 | 2/1998 | ............ A61B 17/04 |
| WO | 99/22648 | 5/1999 | ............ A61B 17/04 |
| WO | 99/53844 | 10/1999 | ............ A61B 17/04 |
| WO | 02/21997 | 3/2002 | ............ A61B 17/04 |
| WO | 03/020137 | 3/2003 | ............ A61B 17/02 |
| WO | 03/049620 | 6/2003 | ............ A61B 17/04 |
| WO | 03/090627 | 11/2003 | ............ A61B 17/04 |
| WO | 2004/082724 | 9/2004 | ............ A61B 17/04 |
| WO | 2008/022250 | 2/2008 | ............ A61B 17/00 |
| WO | 2009/032695 | 3/2009 | ............ A61B 17/04 |
| WO | 2009/114811 | 9/2009 | ............ A61B 17/04 |

OTHER PUBLICATIONS

PCT International Preliminary Examination Report for PCT/US02/38632 3pgs, Jul. 23, 2004.
PCT Search Report and Written Opinion for PCT/US06/20657 7pgs, Mailed Oct. 2, 2007.
European Search Report for EP02791363 4pgs, Mailed Mar. 5, 2007.
UK Search Report for GB 0816111.9 3pgs, Dec. 16, 2008.
UK Search Report for GB 0911011.5 4pgs, Oct. 27, 2009.
UK Search Report for GB 0911013.1 4pgs, Oct. 27, 2009.
UK Search and Examination Report for GB 0911011.5 2pgs, May 28, 2012.
DE Examination Report for DE 102008046561.5 11 pgs, Nov. 16, 2012.

\* cited by examiner

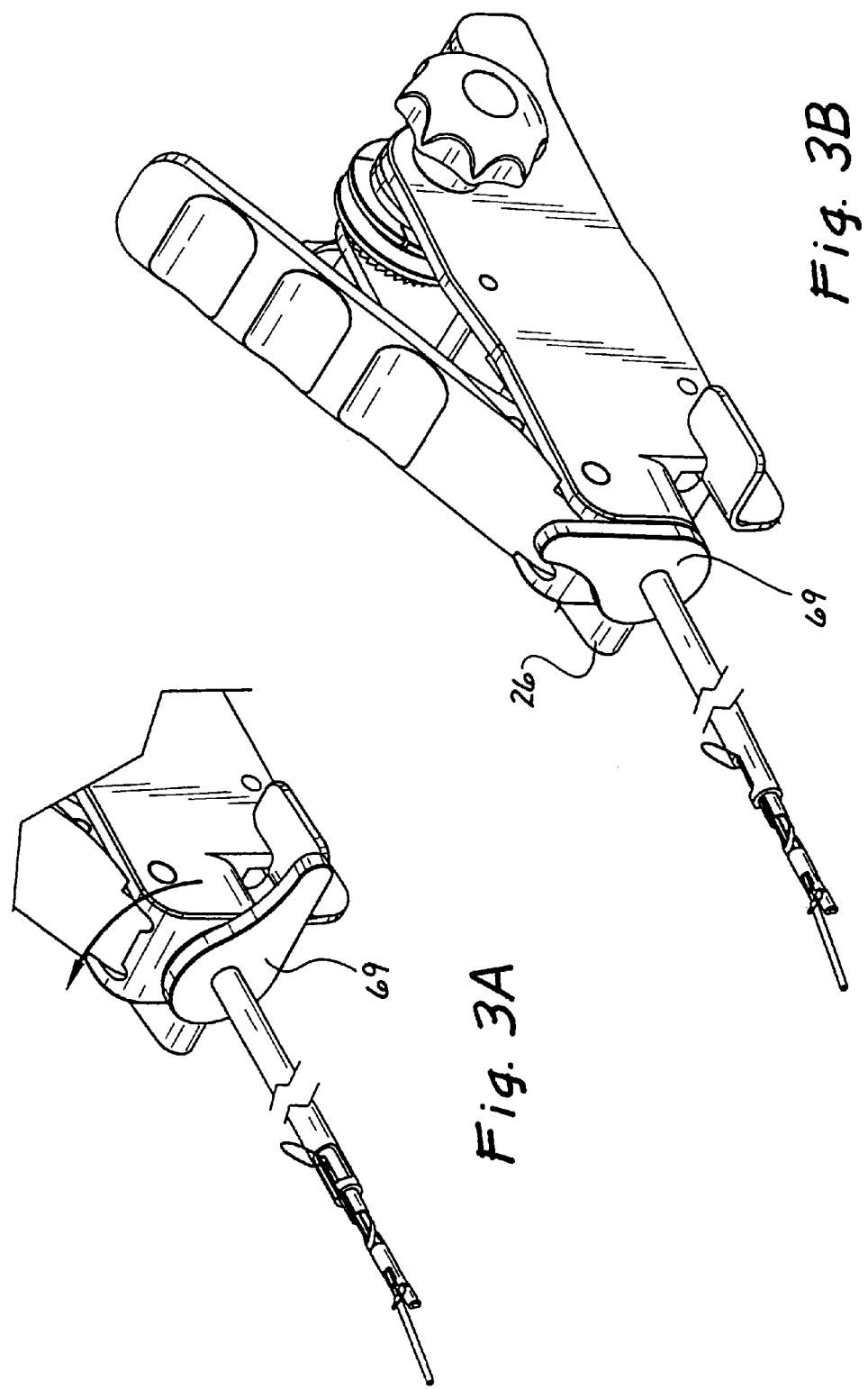

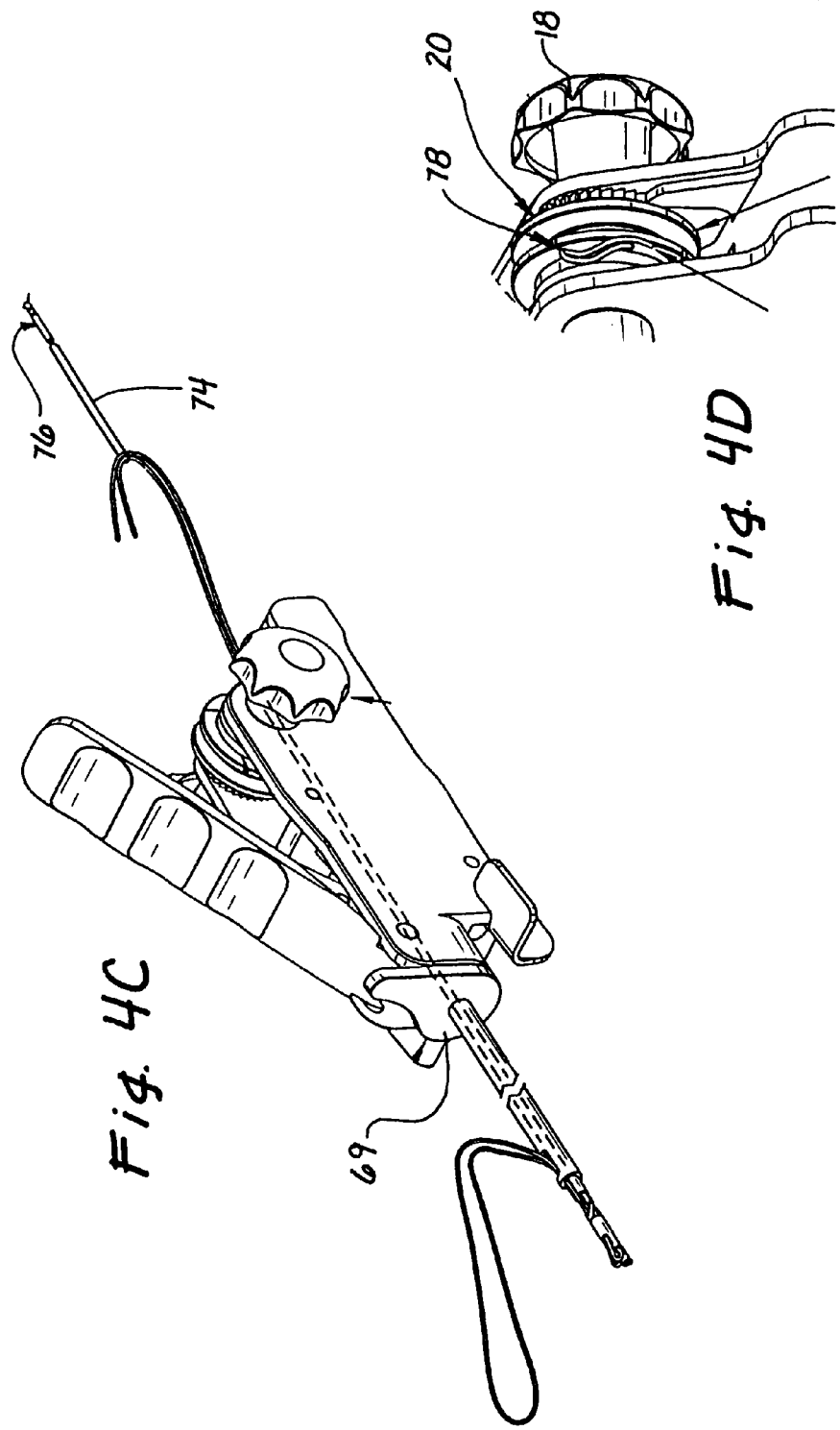

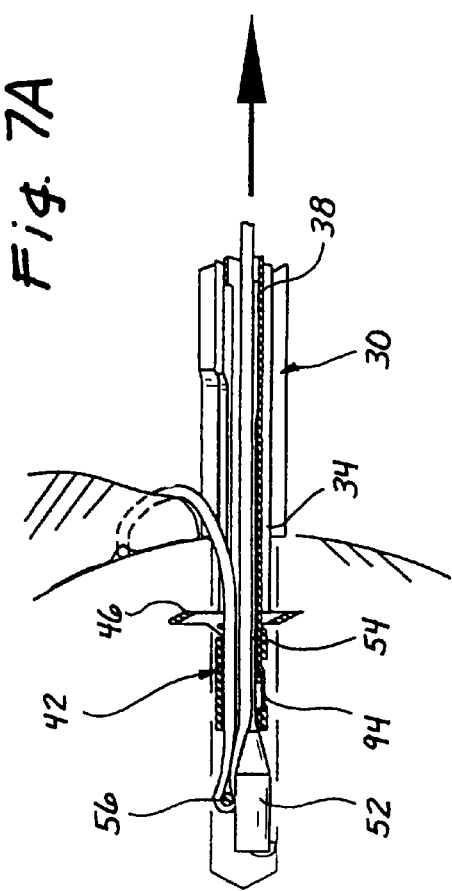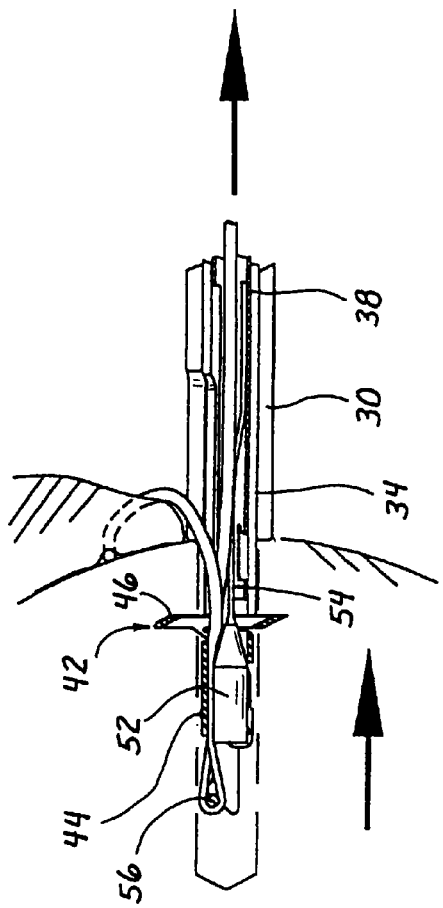

BONE ANCHOR INSERTION DEVICE

CROSS-REFERENCE TO RELATED APPLICATIONS

This application is a continuation of U.S. patent application Ser. No. 10/885,282, filed Jul. 6, 2004, now abandoned, which was a divisional of U.S. patent application Ser. No. 10/077,574, filed Feb. 15, 2002, now U.S. Pat. No. 6,780,198, which claims the benefit, under 35 U.S.C. 119(e), of U.S. Provisional Patent Application No. 60/338,429, filed on Dec. 6, 2001, all of which are incorporated by reference herein.

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it can be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures is of the arthroscopic type, and is considered investigational in nature.

Another significant difficulty with current arthroscopic rotator cuff repair techniques is shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but existing designs suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90B so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

A prior art approach that includes tissue attachment is described in U.S. Pat. No. 5,405,359 to Pierce. In this system, a toggle wedge is comprised of a two piece structure comprising a top portion characterized by the presence of a barbed tip and a bottom portion. The suturing material extends through apertures in each of the two toggle portions, and is maintained in position by means of a knot disposed in the suture at a lower edge of the bottom toggle portion. To anchor the suture into adjacent soft tissue, the two toggle portions are rotated relative to one another, as shown for example in FIG. 33. The disclosure states that the device could be used to anchor suture in bone, as well as soft tissue, if two embodiments are utilized in tandem. However, the system is disadvantageous in that it is complex, difficult to manipulate, and still requires the tying of a knot in the suture.

Another approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrot the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

U.S. Pat. No. 5,782,863 to Bartlett discloses a suture anchor including bone attachment, which simply comprises a conical suture anchor having an anchor bore through which a length of suture is threaded. The anchor is inserted into a bore within a portion of bone using an insertion tool having a shape memory insertion end. As the anchor is inserted, because of its conical shape, it will re-orient itself by rotating in order to fit into the bore, bending the end of the insertion tool. However, once the proximal edge of the bone anchor enters cancellous bone, the shape memory insertion end of the insertion tool will begin resuming its natural straight orientation, thus rotating the anchor back into its original orientation. The corners of the conical body thus protrude into the soft cancellous bone, and the anchor body is prevented from exiting proximally from the bone bore through the hard cortical bone. The insertion tool is then removed.

The Bartlett patent approach, while innovative, is disadvantageous to the extent that it involves the use of a unique and complex insertion tool, and can be difficult to deploy. It also does not permit suturing of the soft tissue prior to anchoring the suture to bone, and thus does not permit tensioning of the suture to approximate the soft tissue to bone, as desired, at the conclusion of the suturing procedure. Additionally, in preferred embodiments, the suture is knotted to the anchor, a known disadvantage.

Yet another prior art approach is disclosed in U.S. Pat. No. 5,961,538 to Pedlick et al. In this patent, a wedge shaped suture anchor system is described for anchoring a length of suture within a bore in a bone portion, which comprises an anchor body having an offset suture opening for receiving the length of suture therethrough, and for creating an imbalance in the rotation of the device as it is inserted. A shaft portion is utilized to insert the wedge-shaped anchor body into the bone bore. Once the anchor body is in cancellous bone, below the cortical bone layer, the shaft is pulled proximally to cause the anchor body to rotate, thereby engaging the corners of the anchor body with the cancellous bone. The shaft then becomes separated from the anchor body, leaving the anchor body in place within the bone.

The Pedlick et al. approach is conventional, in that the suture is attached to desired soft tissue after it is anchored within the bone. Consequently, there is no opportunity to tension the suture, as desired, to optimally approximate the soft tissue to the bone upon completion of the surgical procedure. Additionally, the approach is complex and limited in flexibility, since the suture is directly engaged with the bone anchoring body. There is also the possibility that the bone anchoring body will not sufficiently rotate to firmly become engaged with the cancellous bone before the insertion tool breaks away from the anchor body, in which case it will be impossible to properly anchor the suture.

U.S. Pat. No. 6,056,773 to Bonutti discloses a suture anchoring system which is somewhat similar to that disclosed by Pedlick et al. A cylindrical suture anchor body is provided which is insertable into a bone bore, using a pusher member which pushes distally on the anchor body from a proximal direction. As the anchor body proceeds into the bone bore, below the cortical bone surface, the suture extending through the lumen of the anchor body applies a proximal tensile force on the anchor body, to cause the anchor body to rotate relative to the pusher member, thereby anchoring the anchor body in cancellous bone. Of course, this system has similar disadvantages to those of the Pedlick et al. system, and requires the suture to be directly engaged with the bone anchoring body.

What is needed, therefore, is a new approach for repairing the rotator cuff or fixing other soft tissues to bone, wherein both the bone and suture anchors reside completely below the cortical bone surface, there is no requirement for the surgeon to tie a knot to attach the suture to the bone anchor, and wherein suture tension can be adjusted and possibly measured. The procedure associated with the new approach should better for the patient than existing procedures, should save time, be uncomplicated to use, and be easily taught to practitioners having skill in the art.

SUMMARY OF THE INVENTION

The present invention solves the problems outlined above by providing innovative bone anchor and connective techniques which permit a suture attachment which lies entirely beneath the cortical bone surface, and which further permit the attachment of suture to the bone anchor without the necessity for tying knots, which is particularly arduous and technically demanding in the case of arthroscopic procedures. In particular, the present invention employs a uniquely advantageous handle actuator which facilitates a convenient and efficient procedure for the medical practitioner.

More particularly, there is provided a bone anchor insertion device, comprising a handle, a nosepiece connected to a distal end of the handle, a bone anchor connected to the nosepiece, and an actuator disposed on the handle for deploying the bone anchor, which suture is also fixed to a portion of soft tissue to be attached to a portion of bone. Advantageously, a suture ratchet or tensioning mechanism is disposed in the handle for tensioning suture which is associated with the bone anchor. This mechanism permits precise tensioning, while also permitting one-handed operation, thereby allowing the practitioner to use his or her other hand for other activities, such as camera operation or the like.

In a preferred embodiment, the suture tensioning mechanism comprises a suture knob and a suture ratchet wheel, wherein the suture knob is rotatable to rotate the suture ratchet wheel. The suture ratchet wheel includes a suture fixation slit disposed therein for receiving a free end of the suture. The bone anchor comprises a tubular body which is adapted to receive the suture therethrough.

In another aspect of the invention, there is provided a bone anchor insertion device, comprising a handle, and a nosepiece connected to a distal end of the handle, wherein the nosepiece comprises an outer tube having a suture opening formed in its distal end and an inner tube disposed coaxially within the outer tube. The inner tube includes a longitudinal slot or opening therein, and is fixed relative to the outer tube. A pull tube is provided, which is insertable into the inner tube. A bone anchor is disposed on the pull tube, which includes a laterally deployable member for engaging adjacent bone matter to secure the bone anchor in the bone matter. The inventive device further comprises an actuator disposed on the handle for pulling the pull tube proximally to deploy the laterally deployable member of the bone anchor by engaging the laterally deployable member with a distal end surface of the inner tube. Preferably, the laterally deployable member comprises a toggle ring member.

In preferred embodiments, the inventive bone anchor insertion device further comprises a suture immobilizing member which is associated with the bone anchor for immobilizing a length of suture situated within the bone anchor. The suture immobilizing member, preferably a suture plug, is connected to a distal end of the pull tube, so that further actuation of the actuator on the handle after deployment of the laterally deployable member of the bone anchor causes the suture immobilizing member to move proximally to engage and immobilize the length of suture. A tab is disposed at a distal end of the pull tube for attaching the bone anchor to the pull tube, which tab is designed to break upon continued proximal movement of the pull tube once the laterally deployable member has been completely deployed, so that further proximal movement of the pull tube causes the suture immobilizing member to move proximally.

In still another aspect of the invention, a method for making an orthopedic repair, by re-attaching a portion of soft tissue to a portion of adjacent bone, using a bone anchor insertion device comprising a handle and a nosepiece attached to a distal end of said handle, is described. This method comprises steps of:

a) passing a length of suture through the portion of soft tissue so that a loop of suture is embedded therein;

b) passing a free end of the length of suture through the nosepiece, a bone anchor disposed thereon, and the handle; and c) securing the free end of the length of suture to a suture tensioning mechanism in the handle. Further inventive steps include:

d) locating the bone anchor so that it lies beneath a cortical bone surface of the portion of adjacent bone, preferably by moving the bone insertion device into the vicinity of the repair site through a trocar or the like;

e) deploying the bone anchor so that it remains in place beneath the cortical bone surface; and f) actuating the suture tensioning mechanism to tension the length of suture, thereby approximating the soft tissue portion to the adjacent bone portion as desired.

In a preferred method, the bone anchor insertion device further comprises a pull tube disposed in the nosepiece, and an actuator on the handle for moving the pull tube proximally a desired distance. The bone anchor deployment step further comprises actuating the handle actuator to move the pull tube proximally, until a laterally deployable portion of the bone anchor abuts a mandrel surface on the nosepiece and is thereby forced to laterally deploy. Subsequent to the bone anchor deployment step, a connection between the bone anchor and the pull tube fractures upon continued proximal movement of the pull tube.

Preferably, the bone anchor insertion device further comprises a suture plug attached to a distal end of the pull tube for immobilizing suture within the bone anchor. Thus, the inventive method further comprises a step of continuing to actuate the handle actuator, to thereby move the pull tube proximally, to thereby move the suture plug proximally to immobilize suture within the bone anchor. Then, to complete the procedure, the bone anchor insertion device is separated from the bone anchor and suture plug, the bone anchor insertion device is withdrawn from the repair site, and the suture is trimmed off to complete the repair. The entire method may then be repeated as many times as desired in order to create additional attachment points between the portion of soft tissue and the bone portion, in order to improve the integrity of the effected repair.

In yet another aspect of the invention, there is described a method for making an orthopedic repair, by re-attaching a portion of soft tissue to a portion of adjacent bone, using a bone anchor insertion device comprising a handle and a nosepiece attached to a distal end of said handle. This method comprises the steps of:

a) passing a length of suture through the portion of soft tissue so that a loop of suture is embedded therein;

b) inserting a pull tube, on which is disposed a bone anchor having a laterally deployable member, into the nosepiece;

c) passing a free end of the length of suture through the nosepiece, the bone anchor, and the handle, using snares;

d) locating the bone anchor so that it lies beneath a cortical bone surface of the portion of adjacent bone; and e) actuating an actuator on the handle to move the pull tube proximally, until the bone anchor is engaged with a mandrel surface on the nosepiece and the laterally deployable member is forced to deploy. In preferred approaches, the method further comprises steps of:

f) tensioning the length of suture to approximate the portion of soft tissue to the adjacent portion of bone, as desired;

g) continuing to actuate the actuator on the handle to further move the pull tube proximally, to thereby move a suture plug attached to a distal end of the pull tube proximally to engage and immobilize suture disposed in the bone anchor;

h) separating the bone anchor insertion device from the bone anchor and suture plug;

i) withdrawing the bone anchor insertion device from the repair site; and j) trimming off the suture to complete the repair.

The invention, together with additional features and advantages thereof, may best be understood by reference to the following description taken in conjunction with the accompanying illustrative drawing.

BRIEF DESCRIPTION OF THE DRAWINGS

FIG. 3A is partial perspective view of the handle illustrated in FIG. 3, with the suture support lever in a first position;

FIG. 3B is a perspective view of the handle illustrated in FIGS. 3 and 3A, with the suture support lever in a second position;

FIG. 4C is a perspective view of the bone anchor device of the invention, illustrating the step of removing the long snare loop proximally through the device to tension the suture loop;

FIG. 4D is a perspective view of the suture mechanism of the inventive device;

FIGS. 7A-7B are cross-sectional views in sequence showing further steps in the preferred method of using the inventive bone anchor device to secure soft tissue to adjacent bone;

DESCRIPTION OF THE PREFERRED EMBODIMENT

Figure 1:
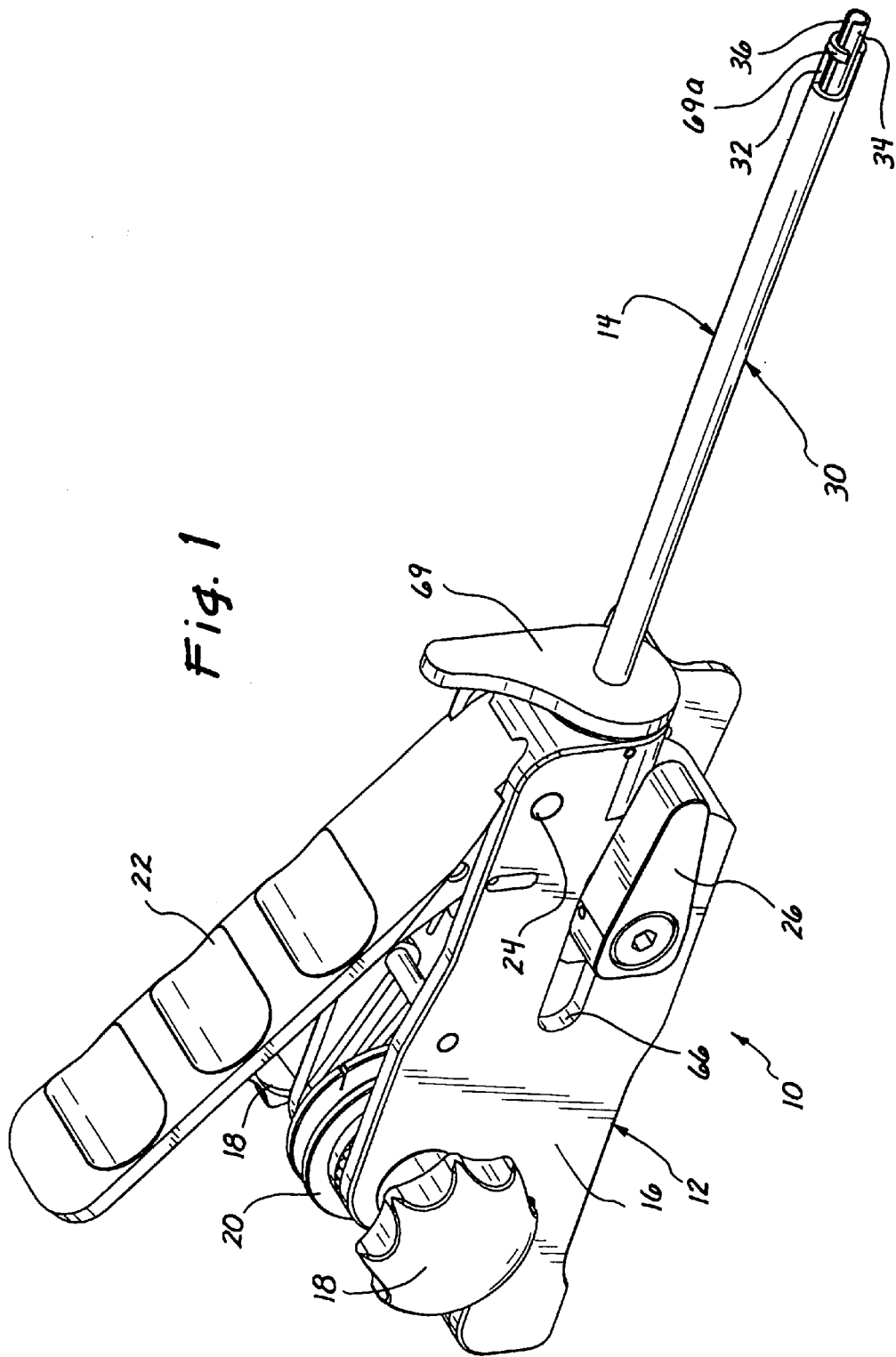
FIG. 1 is a perspective view of a preferred embodiment of the inserter portion of a bone anchor device constructed in accordance with the principles of the present invention.

Referring now more particularly to the drawings, there is shown in FIG. 1 a bone anchor insertion device 10, constructed in accordance with one embodiment of the present invention. The bone anchor insertion device 10 is comprised of an inserter handle 12 and an inserter nosepiece 14, which is attached to a distal end of the handle portion 12. The inserter handle 12 comprises a handle housing 16 which is constructed of a rigid material, such as plastic or metal. The housing is shaped and configured to accommodate a plurality of mechanical components for effecting insertion of a bone anchor during an orthopedic repair procedure, such as the re-attachment of a portion of soft tissue to adjacent bone. Such a procedure may preferably involve a rotator cuff repair procedure.

Figure 2:
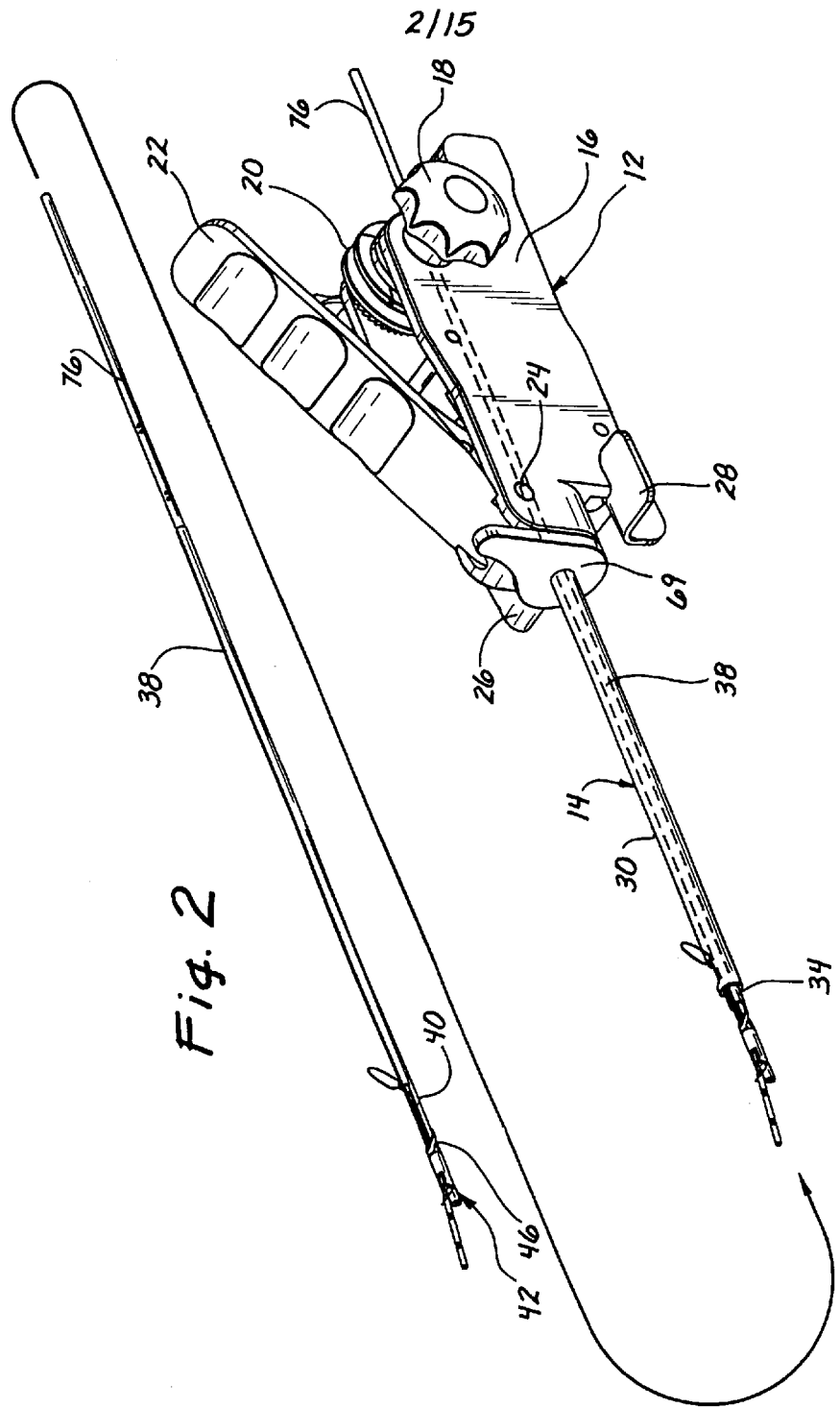
FIG. 2 is a perspective view of a bone anchor device of the present invention, including a bone anchor portion and the inserter portion illustrated in FIG. 1.

More particularly, the aforementioned plurality of mechanical components include, in a preferred embodiment, a suture knob 18, which is rotatably attached to a suture ratchet wheel 20, a hand lever 22 pivotally attached to the housing 16 by means of a pivot pin 24, and an anchor load lever 26. Referring additionally to FIG. 2, it can be seen that the housing 16 also includes a function lever 28. These components will be more particularly described below in conjunction with an explanation of a preferred method for using the bone anchor insertion device 10, and are typically fabricated of a variety of materials, such as plastic, aluminum, or stainless steel.

With reference still to FIGS. 1 and 2, the inserter nosepiece 14 comprises an outer tube 30 having a suture opening 32 formed in its distal end, as shown in FIG. 1. An inner slotted tube 34 is disposed coaxially within the outer tube 30, which, as noted, includes a longitudinal slot or opening 36. The inner tube 34 is preferably fixed relative to the outer tube 30, such that the inner tube 34 is not axially slidable or rotatable relative to the outer tube 30. As will be explained further hereinbelow, the primary function of the inner tube is to act as a mandrel or stop for the purpose of engaging and deploying the bone anchor during the insertion procedure, and the inner tube 34 may be referred to as a die tube for this reason.

As shown in FIG. 2, a pull tube 38 is insertable, in coaxial relationship, into the distal end of the inner slotted tube 34. This pull tube 38, for purposes of illustration, is shown in FIG. 2 separate from the remainder of the device 10, and also in its operable position, inserted from the distal end into the tube 34. When inserted into the tube 34, most of the proximal portion of the pull tube 38 is not visible, and is thus shown in phantom in FIG. 2.

The pull tube 38 is preferably constructed of stainless steel, although other biocompatible materials may be employed as well. A portion of the distal end of the pull tube 38 is constructed such that part of the cylindrical sidewall is cut away, to form a half-cylindrical shape, thereby forming a suture opening 40.

To the distal end of the pull tube 38 is affixed a bone anchor 42 of the type disclosed and described in commonly assigned U.S. patent application Ser. No. 09/876,488, filed Jun. 7, 2001, entitled Method and Apparatus for Attaching Connective Tissues to Bone Using a Knotless Suture Anchoring Device, now U.S. Pat. No. 6,770,076, herein expressly incorporated by reference in its entirety. The bone anchor 42 is best illustrated in FIGS. 6A-8C, and comprises a tubular or cylindrical body 44, which may, for example, be a hypotube, in which a series of diagonal cuts have been made at its proximal end to create an annular generally elliptical angled toggle ring member 46. The cuts may be made by using wire Electro-Discharge Machining (EDM) techniques, though many other suitable known methods and materials for fabricating a generally tubular body and associated proximal toggle ring member may be utilized as well. This toggle ring member 46 is generally oriented diagonally relative to a longitudinal axis 48 of the tubular anchor body 44 (FIG. 6B). The toggle ring member 46 thus formed remains connected to the main portion of the tubular body 44 by two thin struts 50 which are situated such that they are substantially orthogonal to the orientation of the toggle ring member 46, and disposed at an acute angle relative to the longitudinal axis 48.

It is preferred that the anchor 10 be fabricated of biocompatible materials such as 300-series stainless steel (Type 304 or Type 316, for example) or titanium, although suitable bioresorbable plastics may potentially be used as well. In a presently preferred embodiment, the anchor 42 is approximately 11 mm long and 2.8 mm in diameter.

The bone anchor 42 also includes elements comprising a suture anchoring system. For example, as best shown in FIGS. 7A and 7B, a suture plug 52 is disposed at a distal end of the body 42, and is attached at its proximal end to an actuation member 54, which preferably comprises a relatively thin rod or shaft formed of flat ribbon stock, and which extends proximally through the pull tube 38. A pin member 56 is also disposed at the distal end of the body 42, adjacent to the suture plug 52, as shown in FIGS. 7A and 7B, for functioning as a suture return member. This pin member 56 may be journaled or fixedly attached to the sidewall of the body 42, as is disclosed in U.S. patent application Ser. No. 09/876,488, filed Jun. 7, 2001, now U.S. Pat. No. 6,770,076, already incorporated by reference herein.

Now, with reference particularly to FIGS. 6A-8C, as well as FIGS. 4A-4D and 5A-5G, a presently preferred bone and suture anchoring method using the inventive device to reattach soft tissue to bone will be described. As is described in U.S. patent application Ser. No. 09/876,488, filed Jun. 7, 2001, now U.S. Pat. No. 6,770,076, a preferred use for the inventive apparatus is to repair a rotator cuff tendon injury, by reattaching the soft tissue (tendon) 58 to the humerus bone 60. Of course, the inventive apparatus may be used for many other types of orthopedic repairs as well, but rotator cuff repair is representative, and will be described herein.

With reference now to FIGS. 4A-4D and 6A-6D, in particular, a generally tubular trocar (not shown) provides a conduit through the soft tissue of the shoulder for the anchor device of the present invention. Typically, the surgeon makes an incision or stab wound through the outer dermal layers of sufficient size to permit passage of the trocar through skin and the deltoid muscle into proximity with the humeral head 60. Various trocars and techniques for creating the approach passageway are known and may be utilized with the present invention. In addition, more than one incision and conduit may be necessary to perform the several suturing and anchoring steps. Alternatively, some surgeons have been known to dispense with the use of a trocar, and to directly insert instruments through the stab wound and into the shoulder capsule.

Figure 6A:
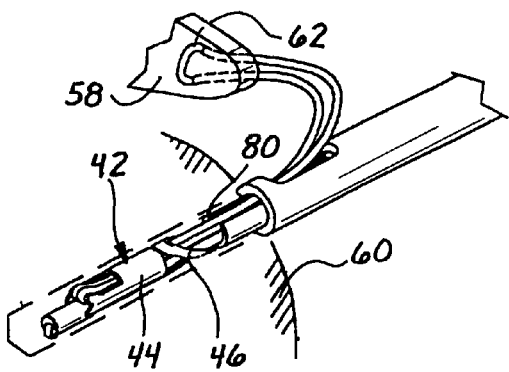
FIGS. 6A-6D are perspective views in sequence showing steps in a preferred method of using the inventive bone anchor device to secure soft tissue to adjacent bone.
Figure 6B:
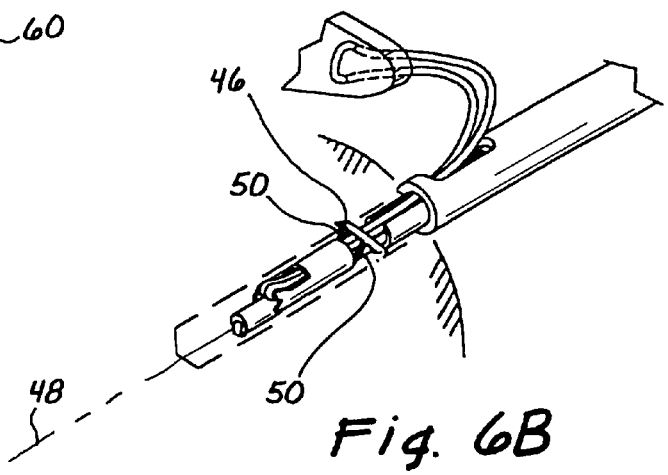

After establishing one or more direct conduits to the humeral head 60, the surgeon passes a length of suture through the soft tissue of the rotator cuff tendon 58 so that a loop 62 of suture material is embedded therein, as seen in FIG. 6A. In preferred approaches, the suture is attached to the soft tissue using a "mattress stitch", which is well known in the art as being a particularly secure stitch which is unlikely to fail postoperatively. Preferably, a suturing instrument is inserted into the trocar to perform the aforementioned suturing step. A preferred suturing approach is taught in U.S. patent application Ser. No. 09/668,055, filed Sep. 21, 2000, entitled Linear Suturing Apparatus and Methods, now U.S. Pat. No. 6,551,330, expressly incorporated herein by reference and commonly assigned herewith. Of course, the inventive devices may also be utilized in an open surgical procedure, if desired, wherein the sutures are manually placed.

Figure 4A:
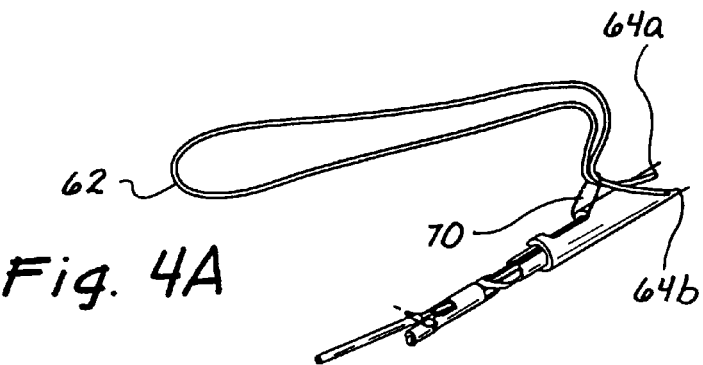
FIG. 4A is a perspective view of the anchor portion of the bone anchor device of the invention, showing the anchor deployment portion of the bone anchor device wherein the short snare has been threaded by a suture loop which is stitched through a piece of soft tissue to be repaired.

Once the suturing process is completed, the free ends 33 of the suture 28 are removed proximally through the trocar from the patient's body, together with the suturing instrument The suture loop 62, without the tissue 58, is shown in FIG. 4A for the purpose of better illustrating the inventive anchoring method. The two free ends 64a, 64b of the length of suture are withdrawn from the patient and coupled to the suture anchor system in a manner to be described.

Figure 3:
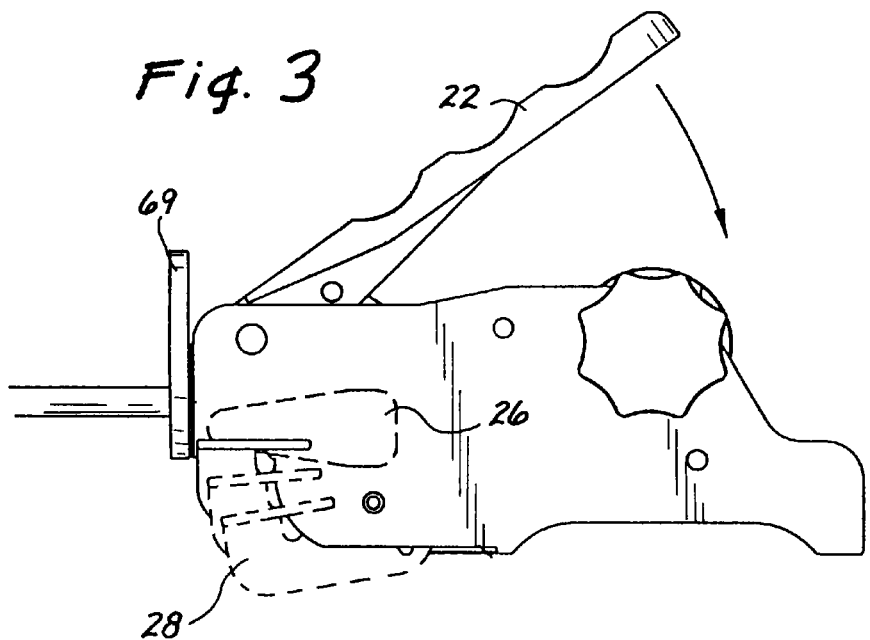
FIG. 3 is a plan view of the handle of the device illustrated in FIGS. 1 and 2.
Figure 5A:
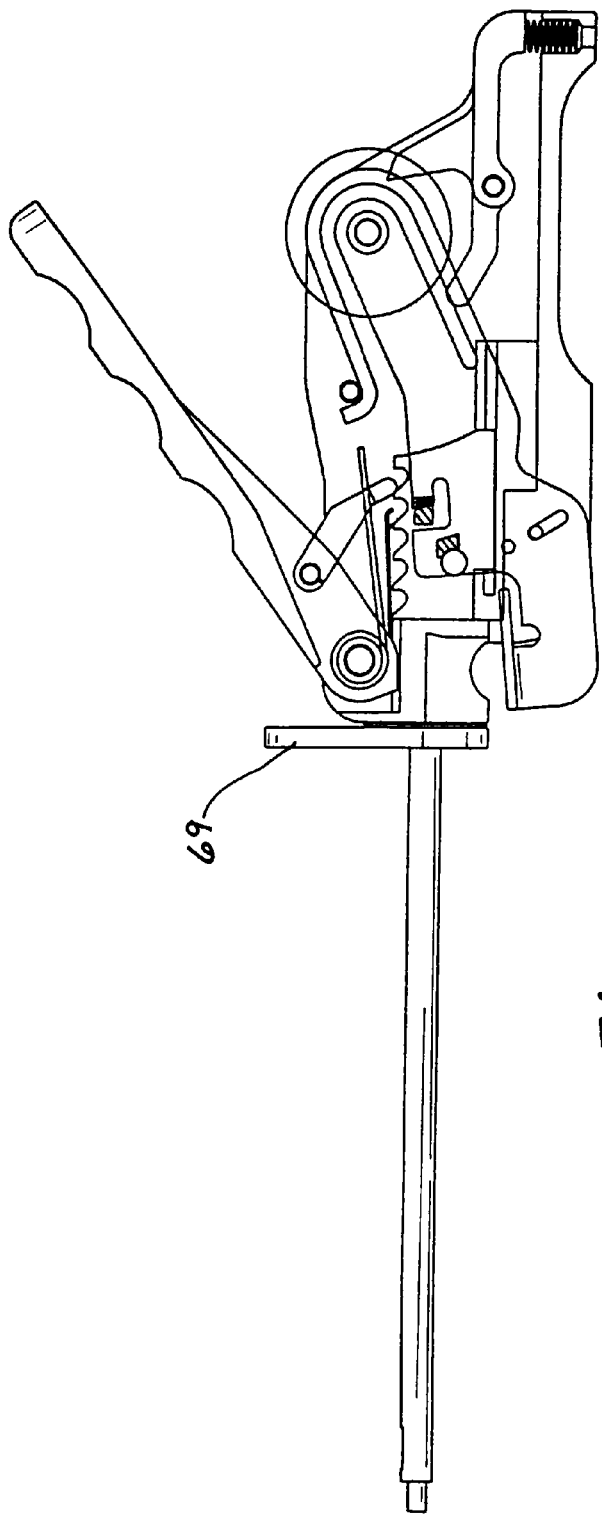
FIGS. 5A-5G are plan schematic views showing the sequential operation of the suture mechanism of the inventive device in a preferred method for using the device.
Figure 5B:
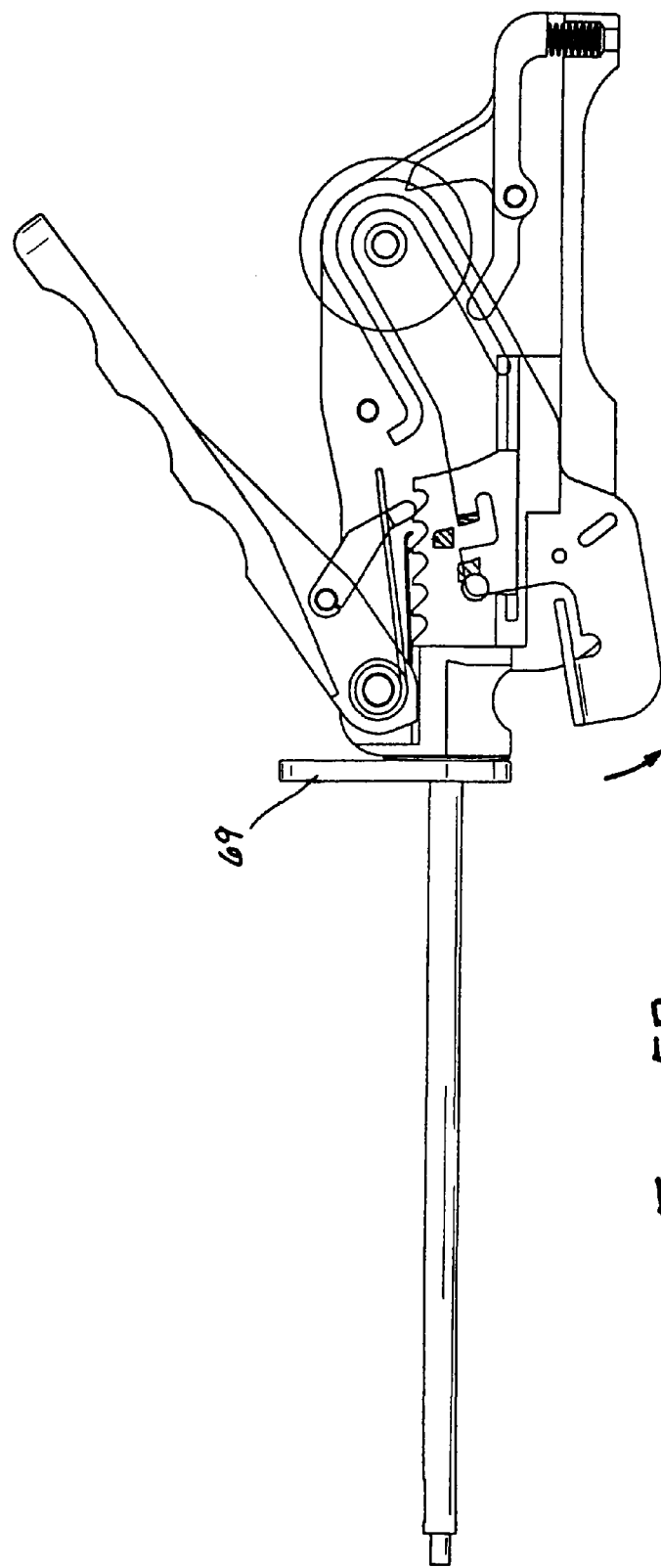
Figure 5C:
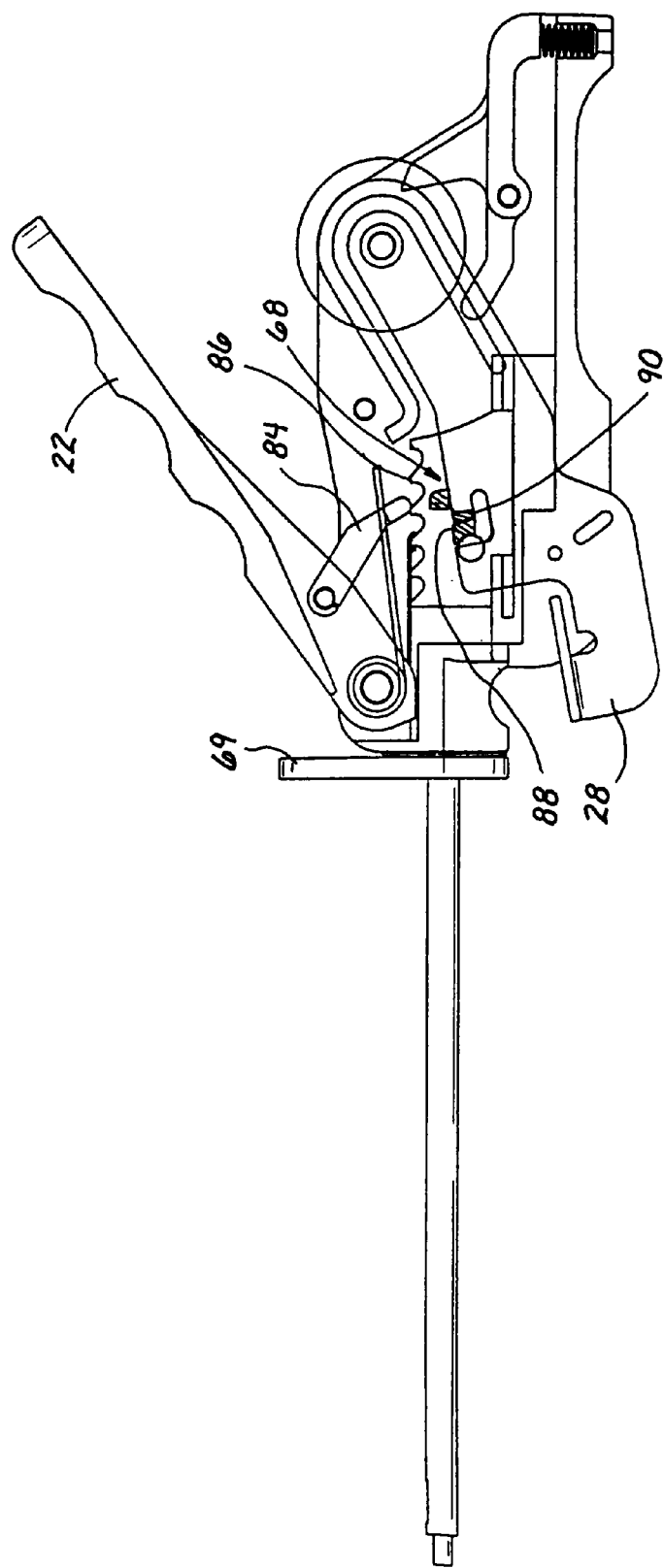
Figure 5D:
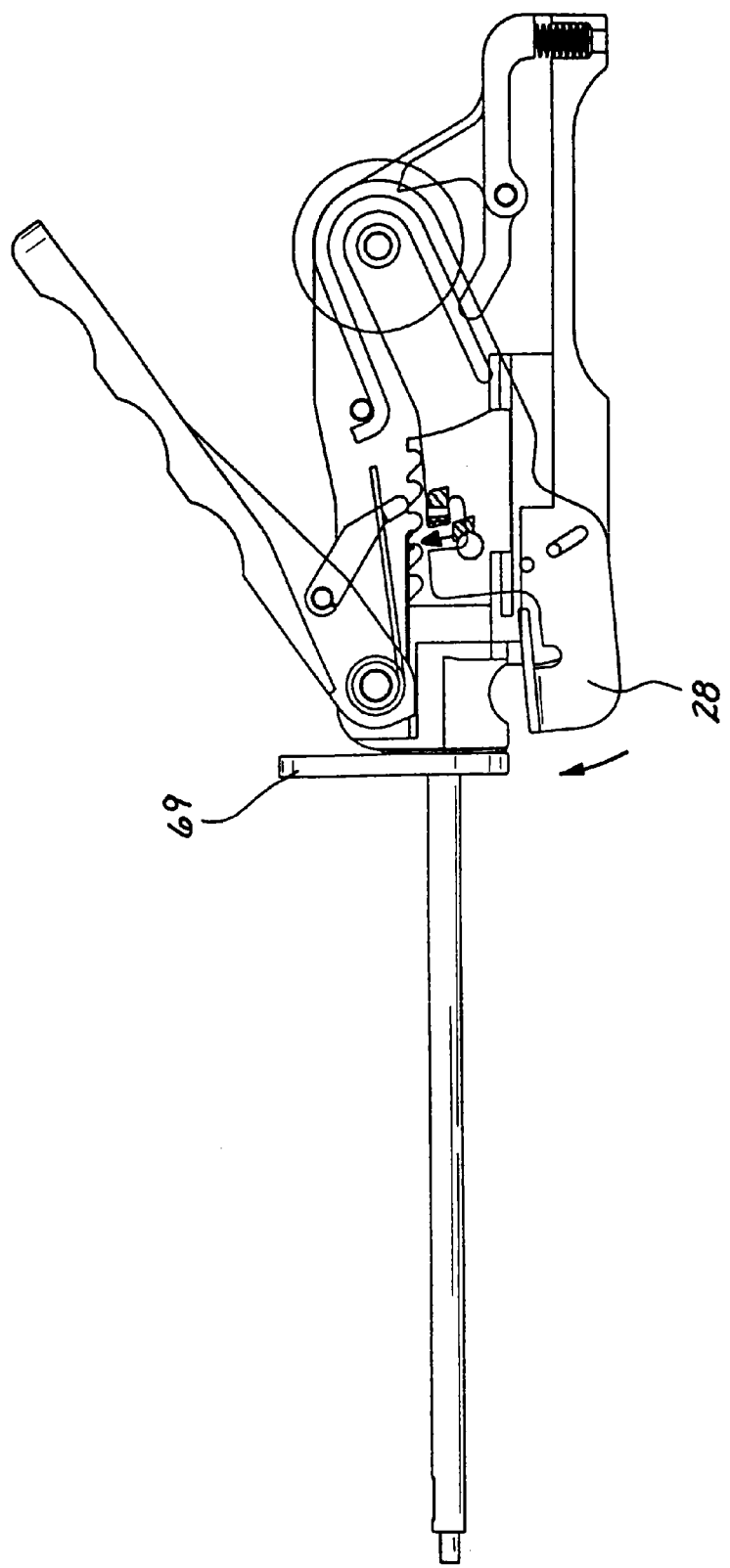
Figure 5E:
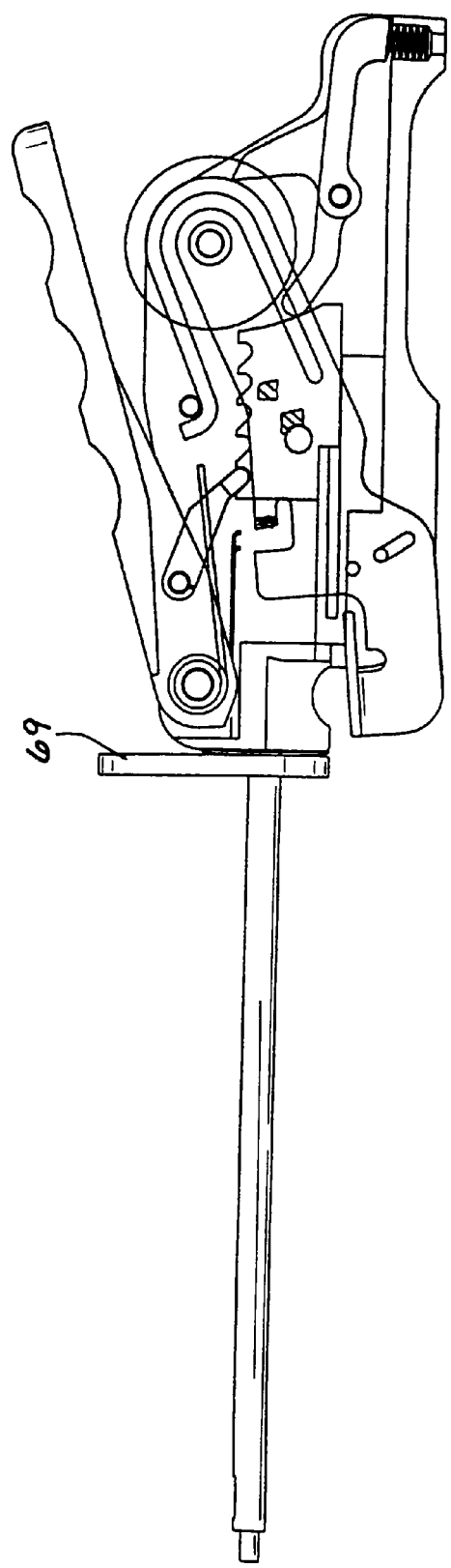

More specifically, at this juncture the pull tube 38 is inserted by the practitioner into the nosepiece 14. The anchor load lever 26 is moved distally through a longitudinal slot or opening 66 in the housing 16, to thus move a rack mechanism 68 distally as well, as shown in FIG. 5G. At this point, the three-position function lever 28 is released by the practitioner. When released, it returns to its center position or "suture lock" position, as shown in FIG. 3. The pull tube 38 may then be inserted proximally through the distal end of the slotted tube or mandrel 34, and into the handle housing 16. The pull tube 38 is properly positioned when the proximal end of the bone anchor 42 abuts the distal end of the mandrel tube 34, as shown in FIGS. 2, 4A, and 6A. The anchor load lever 26 is then rotated in a clockwise direction to tighten a collet (not shown) within the housing 16. When the collet is tightened, the pull tube 38 is longitudinally fixed relative to the inserter nosepiece 14. A suture support lever 69 (FIGS. 1-3) is then actuated to an upper position, as shown in FIG. 1, for example, which causes the outer tube 30 to rotate relative to the inner mandrel tube 34, thereby creating a guiding path for the suture threaded through the device 10 relative to the device. More particularly, this change in position of the suture support lever 69 causes a projecting portion 69a (FIG. 1) of the outer tube 30 to rotate circumferentially to an orientation wherein it lies across the longitudinal slot 36, for the purpose of segregating the suture proximally from the anchor 42, to thereby avoid abrasion of the suture on sharp anchor edges, and to alleviate sharp suture bends in order to ease the process of tensioning the suture, as will be described in greater detail below.

Figure 4B:
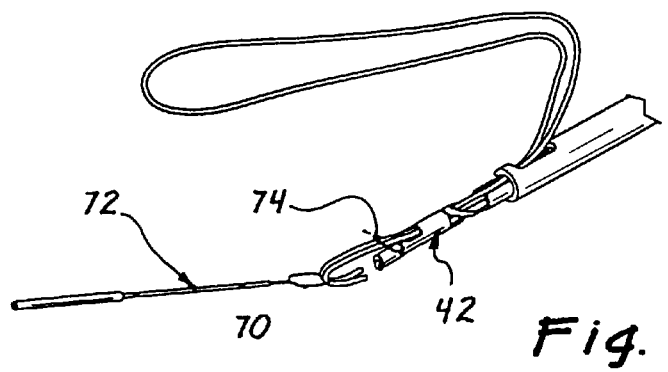
FIG. 4B is a perspective view similar to FIG. 4A, illustrating the next step in the preferred method, wherein the short snare has been removed distally to thread the long snare loop.

With the device outside of the patient's body, the practitioner now threads the free ends 64a, 64b of the suture loop 62 through a loop 70 of a short snare 72, as shown in FIG. 4A. The short snare 72 is then pulled distally out of the bone anchor 42, as shown in FIG. 4B, in the process causing the suture to also be drawn through the anchor 42 and a loop 74 of a long snare 76. The long snare 76 (FIG. 4C) extends through the nosepiece 14, handle 12, and anchor 42, and is then pulled proximally by the practitioner and removed from the device 10 (FIG. 4C). This causes the suture to be threaded through the entire assembly to its proximal end. Most importantly, as shown in FIG. 7A, for example, the suture loop is wrapped about the pin member 56. The suture is then secured to a fixation slit 78 on the suture ratchet wheel 20, as shown in FIG. 4D.

Now, it is time to insert the bone anchor device 10 into a hole 80 which has been previously drilled into the humerus bone 60, as shown in FIG. 6A. The practitioner preferably guides the instrument 10 distally along the suture, using the suture as a kind of guide wire, until the bone anchor 42 is at a desired depth within the hole 80, beneath the cortical bone. At this juncture, the function lever 28 is moved to its lowest position (FIGS. 3A and 5B), which is the "cortical lock" position.

Figure 6C:
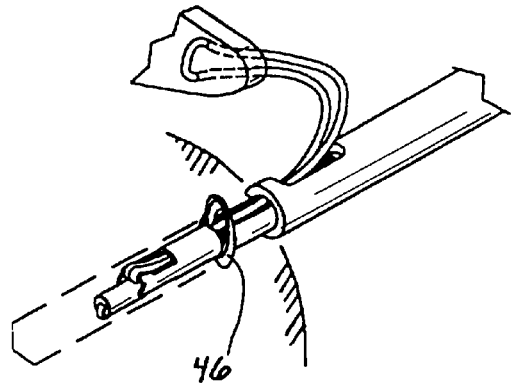
Figure 6D:
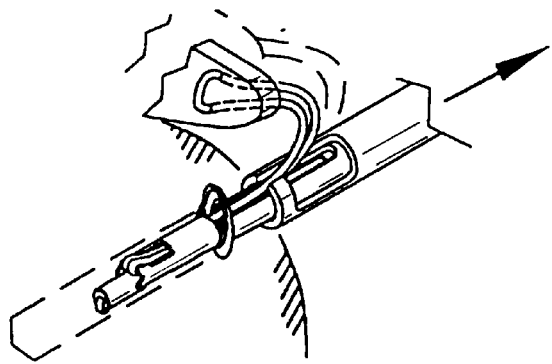

At this point, it is time to deploy the bone anchor toggle ring member 46. This is done by actuating the pivotable hand lever 22 downwardly a desired number of times, which causes a pinion 84 to engage successive teeth 86 on the rack mechanism 68, thereby driving the rack mechanism proximally, and, in turn, drawing the pull tube 38, to which the rack mechanism is attached, proximally. The proximal movement of the pull tube 38 will draw the toggle ring member 46 proximally against the distal end of the mandrel tube 34, thereby causing the thin struts 50 to deform and the toggle ring member to deploy radially, as shown in FIGS. 6B and 6C. As shown in FIG. 5C, because the function lever 28 is in the cortical lock position, a stop 88 is in place to engage a portion 90 of the rack mechanism after the rack has moved proximally a predetermined distance. The purpose of this is to prevent the pull tube 38 from being drawn proximally too far, prior to the upcoming suture tensioning step.

Thus, when the stop 88 has been reached, preventing further actuation of the hand lever 22, the suture support lever 69 is pivoted back to its lower orientation, to release the suture. Then, the suture tensioning step is commenced. This step involves tensioning the suture loop 62 sufficiently to ensure that the soft tissue 58 is approximated, as desired by the practitioner, to the bone 60. The suture is tensioned by rotating the suture knob 18 in order to, in turn, rotate the suture ratchet wheel a desired number of increments, until the desired approximation has occurred, due to tensioning of the suture. This step is illustrated, sequentially, in FIGS. 6D and 7A. The use of the suture ratchet wheel 20 to tension the suture in the present invention is particularly advantageous in that it permits one-handed operation, freeing the other hand for other functions, such as camera operation.

Once the suture tensioning step has been completed, the function lever 28 is returned to the center position, which is the suture lock position (FIG. 3). This step is shown in FIG. 5D, and causes the portion 90 of the rack mechanism 68 to be lifted upwardly above the stop 88, so that the two members are no longer engaged. As a result, the handle 22 may be actuated once again to further draw the pull tube 38 proximally in order to draw the suture plug 52 proximally to lock the suture in place.

Figure 8A:
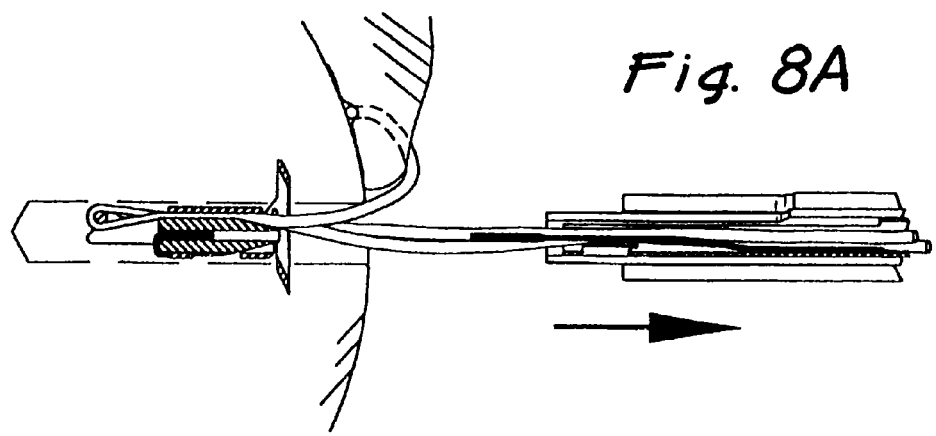
FIGS. 8A-8B are cross-sectional views in sequence showing still further steps in the preferred method illustrated in FIGS. 6A-7B.
Figure 8B:
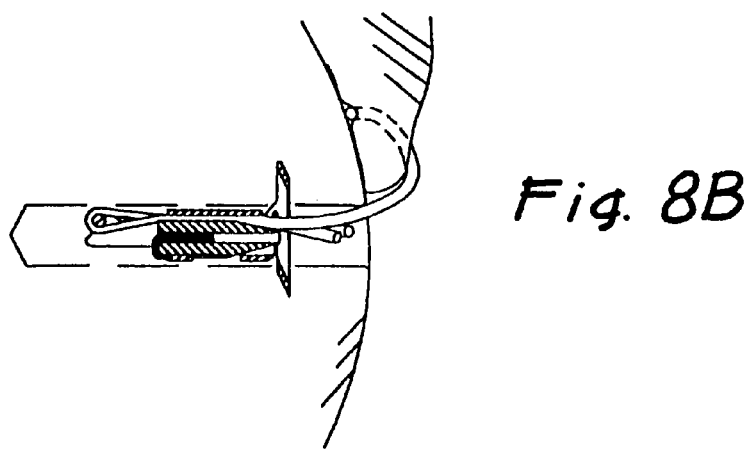
Figure 8C:
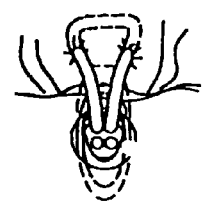
FIG. 8C is an end view illustrating a step of trimming the excess suture at the conclusion of the method shown in FIGS. 6A-8B.

Referring particularly to FIG. 7A, there may be seen a tab 94 formed at the end of the pull tube 38 and attached by welding or other suitable means to the anchor 42. Since the toggle ring 46 has been completely deployed and now abuts the mandrel tube 34, further pulling on the pull tube 38 serves to fracture the attachment of the pull tube 38 to the anchor 42 at the tab 94, and thus transforms the distal to proximal movement of the pull tube 38 into a direct linear translation of the suture plug 52, via the actuation member 54. The practitioner will therefore actuate the hand lever 22 accordingly, to draw the suture plug 52 proximally, as shown in FIG. 7B, such that the suture is immobilized, as shown, between the suture plug and the adjacent walls of the anchor body 44. FIG. 5E illustrates the continued movement of the rack mechanism 68, responsive to continued actuation of the handle 22, to retract the suture plug. Because of the design of the actuation member 54, which attaches the pull tube 38 to the suture plug 52, to include a predetermined fracture point, continued actuation of the handle 22 after the suture plug has immobilized the suture in place will cause the actuation member 54 to fracture, thereby separating the device 10 from the anchor body 44. The device 10 may then be withdrawn proximally from the procedural site, as shown in FIG. 8A, and the sutures trimmed, as shown in FIGS. 8B and 8C.

Figure 5F:
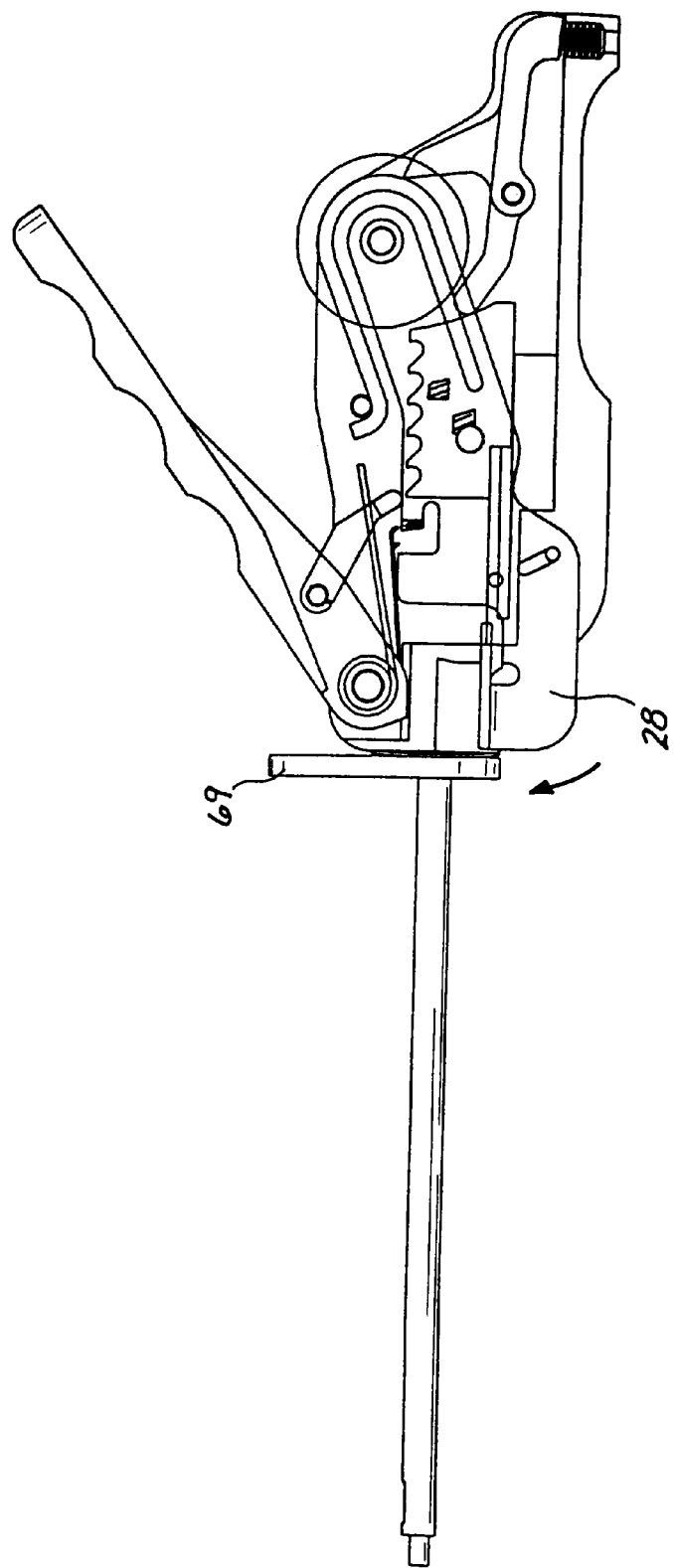
Figure 5G:
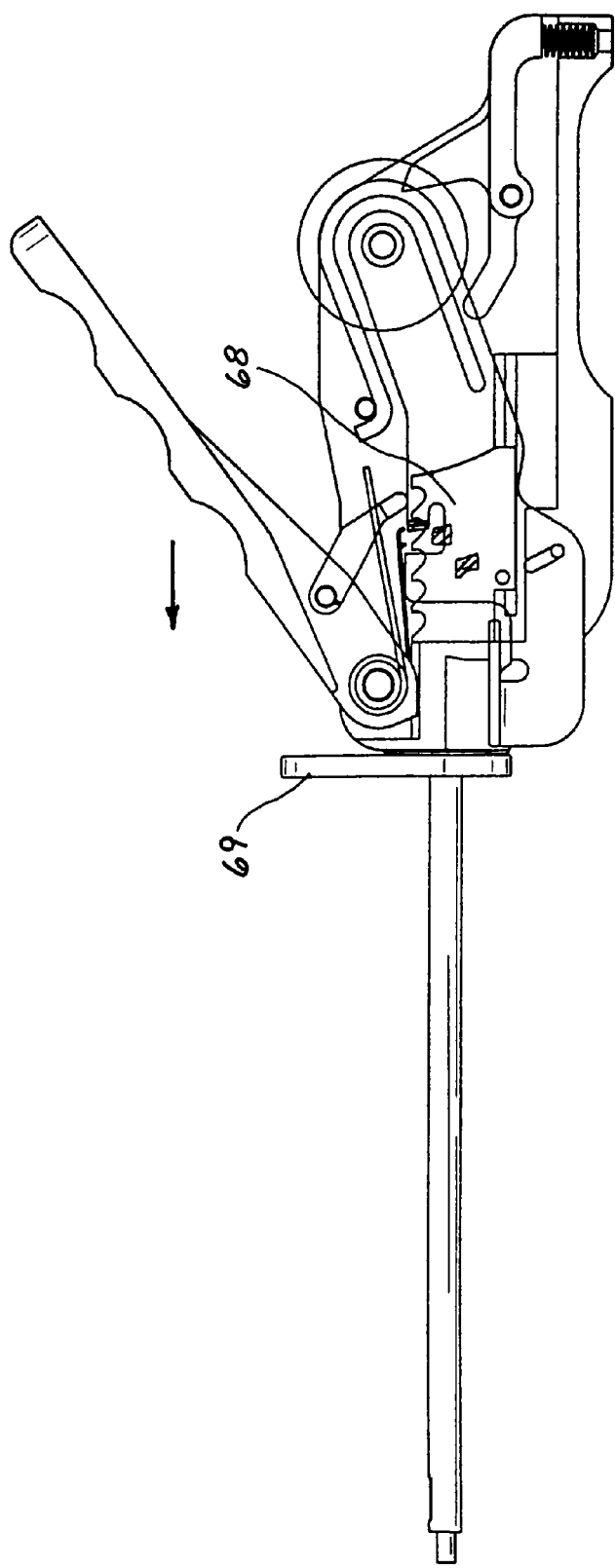

FIGS. 5F and 5G illustrate, sequentially, the steps for reloading the driver 10, in the event that more than one suture is desired (as will be typically the case). To reload the driver, a new pull tube is inserted into the driver device 10, as shown, in a manner substantially identical to that described above, and all of the foregoing procedural steps may be repeated as many times as desired.

Preferably, the driver device 10 is constructed to be a reusable device, and the pull tube and anchor portions are disposable. However, it is possible to construct the driver device 10 to be disposable as well, if desired.

It is to be understood that the disclosed invention is applicable to many different types of procedures involving, in particular, the attachment of connective or soft tissue to bone. It is also to be understood that the specific mechanisms disclosed herein may be modified, using substantially equivalent mechanisms, within the skills of those of ordinary skill in the art, to effect the same or similar mechanical movements and functions. All of the terms used herein are descriptive rather than limiting, and many changes, modifications, and substitutions may be made by one having ordinary skill in the art without departing from the spirit and scope of the invention. The scope of the invention is, therefore, indicated by the appended claims rather than by the foregoing description. All changes which come within the meaning and range of equivalency of the claims are to be embraced within their scope.

What is claimed is:

1. A method for making an orthopedic repair, by re-attaching a portion of soft tissue to a portion of adjacent bone, using a bone anchor insertion device comprising a handle and a nosepiece attached to a distal end of said handle, said method comprising:
   passing a length of suture through said portion of soft tissue so that a loop of suture is embedded therein;
   threading free ends of the length of suture through a first snare, the first snare extending from the nosepiece; wherein the first snare is coupled to a second snare that extends through the nosepiece, a bone anchor and the handle, the second snare further engaged with a suture tensioning mechanism in the handle;
   pulling the second snare through the device to thereby cause the free ends of the length of suture to be threaded through the nosepiece, the bone anchor and the handle; and
   securing the free ends of the length of suture to the suture tensioning mechanism in the handle;
   locating said bone anchor so that it lies beneath a cortical bone surface of said portion of adjacent bone;
   deploying said bone anchor so that it remains in place beneath said cortical bone surface;
   actuating said suture tensioning mechanism to tension said length of suture, thereby approximating said soft tissue portion to said adjacent bone portion and said bone anchor as desired.

2. The method of claim 1 wherein the suture tensioning mechanism comprises a suture knob and a suture ratchet wheel, wherein the suture ratchet wheel comprises a suture fixation slit, and wherein securing the free ends of said length of suture further comprises securing said free ends of said length of suture to said suture fixation slit.

3. The method of claim 2 wherein actuating said suture tensioning mechanism comprises rotating said suture knob to thereby rotate said suture ratchet wheel.

4. The method of claim 2 wherein the suture tensioning mechanism further comprises a release such that the tension on the length of suture may be made loose, reversed, or set free.

5. The method of claim 1 further comprising breaking a tab disposed at a distal end of a pull tube, the tab connecting the pull tube and the bone anchor, whereby the pull tube may be moved proximally from the cortical bone surface.

6. The method of claim 5, wherein the bone anchor insertion device further comprises an actuator on the handle for moving the pull tube proximally or distally a desired distance, the bone anchor deployment step further comprising actuating the handle actuator to move the pull tube relative to a mandrel until a laterally deployable portion of the bone anchor abuts a mandrel surface on the nosepiece and is thereby forced to laterally deploy.

7. The method of claim 6, wherein the bone anchor further comprises a suture plug for immobilizing the length of suture within the bone anchor, the suture plug attached to an actuation member extending from the pull tube, the method further comprising:
   continuing to actuate the handle actuator to thereby move the actuation member proximally, thereby moving the suture plug proximally to immobilize the length of suture within the bone anchor.

8. The method of claim 7, wherein immobilizing the length of suture within the bone anchor comprises compressing the length of suture between the suture plug and a body of the bone anchor.

9. The method of claim 7, further comprising:
   separating the bone anchor insertion device from the bone anchor and the suture plug;
   withdrawing the bone anchor insertion device from the repair site; and
   trimming off the length of suture to complete the repair.

10. The method of claim 1, wherein the steps of threading free ends of the length of suture through the bone anchor and pulling the snare further comprises wrapping the length of suture about a pin member disposed at a distal end of the bone anchor.

11. The method of claim 1, wherein the first snare extends from a lateral aperture in the nosepiece disposed proximally relative to a nosepiece distal end.

12. A method for making an orthopedic repair, by re-attaching a portion of soft tissue to a portion of adjacent bone, using a bone anchor insertion device comprising a handle and a nosepiece attached to a distal end of said handle, said method comprising:
   passing a length of suture through said portion of soft tissue so that a loop of suture is embedded therein;
   threading free ends of the length of suture through a first snare, the first snare extending from the nosepiece; wherein the first snare is coupled to a second snare that extends through the nosepiece, a bone anchor and the handle, the second snare further engaged with a suture tensioning mechanism in the handle;
   pulling the second snare through the device to thereby cause the free ends of the length of suture to be passed through the nosepiece, the bone anchor and the handle; and
   securing the free ends of the length of suture to the suture tensioning mechanism in the handle, wherein the suture tensioning mechanism comprises a suture knob and a suture ratchet wheel, wherein the suture ratchet wheel comprises a suture fixation slit, and wherein securing the free ends of said length of suture further comprises securing said free ends of said length of suture to said suture fixation slit;

locating said bone anchor so that it lies beneath a cortical bone surface of said portion of adjacent bone;

deploying said bone anchor so that it remains in place beneath said cortical bone surface;

actuating said suture tensioning mechanism to tension said length of suture, thereby approximating said soft tissue portion to said adjacent bone portion and said bone anchor as desired, wherein actuating said suture tensioning mechanism comprises rotating said suture knob to thereby rotate said suture ratchet wheel.

13. The method of claim 12, wherein the step of threading free ends of the length of suture through the bone anchor further comprises wrapping the length of suture about a pin member disposed at a distal end of the bone anchor.

14. The method of claim 12 further comprising breaking a tab disposed at a distal end of a pull tube associated with the bone anchor, the tab connecting the pull tube and the bone anchor, whereby the pull tube may be moved proximally from the cortical bone surface.

15. The method of claim 14, wherein the bone anchor insertion device further comprises an actuator on the handle for moving the pull tube proximally or distally a desired distance, the bone anchor deployment step further comprising actuating the handle actuator to move the pull tube relative to a mandrel until a laterally deployable portion of the bone anchor abuts a mandrel surface on the nosepiece and is thereby forced to laterally deploy.

16. The method of claim 15, wherein the bone anchor further comprises a suture plug for immobilizing the length of suture within the bone anchor, the suture plug attached to an actuation member extending from the pull tube, the method further comprising:

continuing to actuate the handle actuator to thereby move the actuation member proximally, thereby moving the suture plug proximally to immobilize the length of suture within the bone anchor.

17. The method of claim 16, wherein immobilizing the length of suture within the bone anchor comprises compressing the length of suture between the suture plug and a body of the bone anchor.

18. The method of claim 17, further comprising:
separating the bone anchor insertion device from the bone anchor and the suture plug;
withdrawing the bone anchor insertion device from the repair site; and
trimming off the length of suture to complete the repair.

19. The method of claim 12, wherein the suture tensioning mechanism further comprises a release such that the tension on the length of suture may be made loose, reversed, or set free.

20. The method of claim 12, wherein the step of actuating comprises incrementally tensioning the length of suture to approximate the tissue to bone.

21. The method of claim 12, wherein the step of actuating is performed single-handedly.

22. The method of claim 12, wherein the bone anchor is disposed on a distal end of the nosepiece.

23. The method of claim 22, wherein the first snare extends from an aperture spaced proximally relative to the distal end of the nosepiece.

* * * * *